United States Patent
Shaikenov et al.

(10) Patent No.: US 6,262,110 B1
(45) Date of Patent: Jul. 17, 2001

(54) FARNESYL-PROTEIN TRANSFERASE INHIBITORS

(75) Inventors: Tattym E. Shaikenov, Almaty; Sergazy M. Adekenov, Karaganda, both of (KZ)

(73) Assignee: International Phytochemistry Research Labs, Ltd., Virginia Beach, VA (US)

(*) Notice: Subject to any disclaimer, the term of this patent is extended or adjusted under 35 U.S.C. 154(b) by 0 days.

(21) Appl. No.: 09/360,834

(22) Filed: Jul. 26, 1999

Related U.S. Application Data

(60) Division of application No. 09/030,300, filed on Feb. 25, 1998, now Pat. No. 6,051,565, which is a continuation-in-part of application No. 08/934,229, filed on Sep. 19, 1997, now Pat. No. 5,902,809, and application No. 08/934,228, filed on Sep. 19, 1997, and application No. 08/934,471, filed on Sep. 19, 1997
(60) Provisional application No. 60/051,681, filed on Jul. 3, 1997.

(51) Int. Cl.$^7$ .................. A61K 31/34; C07D 307/93
(52) U.S. Cl. ........................... 514/468; 549/299
(58) Field of Search .................. 514/468; 549/297, 549/298, 299

(56) References Cited

U.S. PATENT DOCUMENTS

| | | | |
|---|---|---|---|
| 5,578,637 | 11/1996 | Lai et al. | 514/450 |
| 5,602,171 | 2/1997 | Tang et al. | 514/455 |
| 5,610,173 | 3/1997 | Schwartz et al. | 514/378 |
| 5,614,642 | 3/1997 | Tang et al. | 549/389 |
| 5,631,280 | 5/1997 | Ciccarone et al. | 514/416 |
| 5,650,415 | 7/1997 | Tang et al. | 514/312 |
| 5,663,196 | 9/1997 | Sari et al. | 514/468 |
| 5,700,823 | 12/1997 | Hirth et al. | 514/380 |

FOREIGN PATENT DOCUMENTS

| | | |
|---|---|---|
| 7-206839 | 8/1995 | (JP). |
| N-931984 | 8/1993 | (KZ). |
| 1185 | 12/1993 | (KZ). |
| 1186 | 12/1993 | (KZ). |
| 1187 | 12/1993 | (KZ). |
| 1188 | 12/1993 | (KZ). |
| 1189 | 12/1993 | (KZ). |
| 1190 | 12/1993 | (KZ). |
| 1192 | 12/1993 | (KZ). |
| 1193 | 12/1993 | (KZ). |
| 909 | 6/1994 | (KZ). |
| 1746674 | 3/1992 | (SU). |

OTHER PUBLICATIONS

Barnah et al., Phytochemistry, vol. 36(1), pp. 29–36, 1994.*
Picman et al., Biochem. Syst. Ecol., vol. 11 (4) pp. 321–327, 1983.*
Plutno et al., Khim. Prir. Soedin., vol. 5, pp. 687–693, 1995.*
Koveeda et al., Yakugaku Zasshi, vol. 108 (5), 458–460, 1988.*
Waddell et al., J. Pharmaceu. Sci., vol. 68(6), 715–18, 1979.*
Barbacid, ras Genes, Ann. Rev. Biochem., vol. 56, pp. 779–827 (1987).
Gibbs et al., "Intrinsic GTPase activity distinguishes normal and oncogenic ras p21 molecules", Proc. Natl. Acad. Sci. USA, vol. 81, pp. 5704–5708 (Sep. 1984).
Jung et al., "Two Types of RAS Mutants That Dominantly Interfere with Activators of RAS", Mol. Cell. Biol., vol. 14, No. 6, pp. 3707–3718 (Jun. 1994).
Marom et al., "Selective Inhibition of Ras–dependent Cell Growth by Farnesylthiosalisylic Acid", J. Biol. Chem., vol. 270, No. 38, pp. 22263–22270 (1995).
Prendergast et al., "Farnesyltransferase Inhibition Causes Morphological Reversion of ras–Transformed Cells by a Complex Mechanism That Involves Regulation of the Actin Cytoskeleton", Mol. Cell. Biol., vol. 14, No. 6, pp. 4193–4202 (Jun. 1994).
Shears et al., "Characterization of a rapid cellular–fractionation technique for hepatocytes, Application in the measurement of mitochondrial membrane potential in situ", Biochem. J., vol. 219, pp. 375–382 (1984).
Vogt et al., "A Non–peptide Mimetic of Ras–CAAX: Selective Inhibition of Farnesyltransferase and Ras Processing:", J. Biol. Chem., vol. 270, No. 2, pp. 660–664 (1995).
Adekenov et al., Sesquiterpene lactones from *Artemisia glabella*, Fitoterapia, vol. LXVI, No. 2, pp. 142–146 (1995).
Bottex–Gauthier et al., "In Vitro Biological Activities of Arglabin, A Sesquiterpene Lactone from the Chinese Herb *Artemisia myriantha* Wall. (Asteraceae)", Biotechnology Therapeutics, 4 (1&2), pp. 77–98 (1993).
Epstein et al., "Quantitation of prenylcysteines by a selective cleavage reaction", Proc. Natl. Acad. Sci. USA, vol. 88, pp. 9668–9670 (Nov. 1991).
Adekenov et al., "Reactions at the double bond and epoxy group of arglabin," Khim. Prir. Soedin., No. 1, pp. 33–42 (1991).
Ito et al., "Seven Sesquiterpene Lactones from Inula Britannica Var. Chinensis," Phytochemistry, vol. 20, pp. 271–273 (1981).
Rigby et al., "Total Synthesis of (±)–Grosshemin", J. Am. Chem. Soc. vol. 109, pp. 3147–3149 (1987).
The Merck Index, 10th Edition, pp. 329, 394, 408, 599, 1427 and 1428 (1983).

(List continued on next page.)

*Primary Examiner*—Joseph K. McKane
*Assistant Examiner*—Taofiq A. Solola
(74) *Attorney, Agent, or Firm*—W. Jackson Matney, Jr.; Milbank, Tweed, Hadley & McCloy LLP

(57) ABSTRACT

Substantially pure preparations of phosphosesquiterpenes are described. The compounds inhibit farnesyl-protein transferase activity and are useful for the treatment of cancer. Methods for inhibiting fanesyl-protein transferase activity are also described.

2 Claims, 20 Drawing Sheets

OTHER PUBLICATIONS

Gibbs et al., "The Potential of Farnesyltransferase Inhibitors as Cancer Chemotherapeutics," Ann. Rev. of Pharmacol. Toxicol., vol. 37, pp. 143–166 (1997).

Woerdenbag et al., "Progress in the research of artemisinin–related antimalarials: an update," Pharmacy World & Science, vol. 16, No. 4, pp. 169–181 (1994).

Lerner et al., "Inhibition of Ras prenylation: a signaling target for novel anti–cancer drug design", Anti–Cancer Drug Design, vol. 12, No. 4, pp. 229–238 (1997).

Omer et al., "Farnesyl: proteintransferase inhibitors as agents to inhibit tumor growth," BioFactors, vol. 6, No. 3, pp. 359–366 (1997).

Kelloff et al., "Farnesyl Protein Transferase Inhibitors as Potential Cancer Chemopreventatives," Cancer Epidemiology Biomarkers & Prevention, vol. 6, No. 4, pp. 267–282 (Apr. 1997).

Messier et al., "High Throughput Assays of Cloned Adrenergic, Muscarinic, Neurokinin, and Neurotrophin Receptors in Living Mammalian Cells," Pharmacology & Toxicology, vol. 76, No. 5, pp. 308–311 (May 1995).

Gibbs et al., "Farnesyltransferase inhibitors and anti–Ras therapy", Breast Cancer Research and Treatment, vol. 38:, pp. 75–83, (1996).

Brauner–Osborne et al., "Pharmacology of muscarinic acetylcholine receptor subtypes (m1–m5): high throughput assays in mammalian cells," European Journal of Pharmacology, vol. 295, pp. 93–102 (1996).

Bork et al., "Sesquiterpene lactone containing Mexican Indian medicinal plants and pure sesquiterpene lactones as potent inhibitors of transcription factor NF–KB", FEBS Letters 402, pp. 85–90 (1997).

Zhuzbaev et al., "Approaches to the total synthesis of sesquiterpenoids of the guaiane series," Russian Chemical Reviews vol. 64, No. 2, pp. 187–200 (1995).

Veselovskii et al., "A novel approach to the synthesis of regular monocyclopentanoids of the sesquiterpene series", Khim. Prir. Soedin, No. 3 (1992).

Moiseenkov et al., "New synthesis of guaiane sesquiterpenoids based on trans–3–isopropenyl–2–(2'–carbomethoxyethyl)cyclopentan –1–one", Khim. Prir. Soedin, No. 1, pp. 126–131 (1993).

Giordano et al., "The Gastric Cytoprotective Effect of Several Sesquiterpene Lactones," Journal of Natural Products, vol. 53, No. 4, pp. 803–809, (Jul.–Aug. 1990).

Blanco et al., "A novel activity for a group of sesquiterpene lactones: inhibition of aromatase", FEBS Letters 409, pp. 396–400 (1997).

Guardia et al., "Mucus Synthesis and Sulfhydryl Groups in Cytoprotection Mediated by Dehydrolecodine, a Sesquiterpene Lactone," Journal of Natural Products, vol. 57, No. 4, pp. 507–509 (Apr. 1994).

Adekenov et al., "Arglabin—A New Sesquiterpene Lactone From Artemisia Glabella", Khim. Prir. Soedin., No. 5, pp. 655–656 (1982).

Adekenov et al., "1β, 10α–Dihydroxyarglabin—A New Sesquiterpene Lactone From *Artemisia glabella*", Chemistry of Natural Compounds, vol. 29, No. 6, pp. 735–739 (1993).

Adekenov et al., "The Chemistry of Sesquiterpene Lactones", Alma–Alta:Gylym, pp. 1–188 (1990).

* cited by examiner

Figure 1

| #carbon | Guaianolide | 1 | 2 | 3 | 4 | 5 | 6 | 8 | 9 | 10 | 11 | 12 | 13 |
|---|---|---|---|---|---|---|---|---|---|---|---|---|---|
| C1 | CH | C | C | C | CE | C | CH | COH | COH | C | CE | CE | C |
| C2 | CH2 | CO | CO | CO | CH2 | CE | CH2 | CH2 | CH2 | CH | CHE | CHE | CH |
| C3 | CH2 | CH | CH | CH | CH | CHE | CHE | CH | CH | CH | CHE | CHE | CH |
| C4 | CH | C | C | C | C | COH | CE | C | C | COH | COH | COH | COH |
| C5 | CH | CH | CH | CH | CH | CH | CH | CH | CH | CH | CH | CH | CH |
| C6 | CHL | Cpp | Cpp | Cpp | Cpp | Cpp | Cpp | Cpp | Cpp | Cpp | Cpp | Cpp | Cpp |
| C7 | CH | CH | CH | CH | CH | CH | CH | CH | CH | CH | CH | CH | CH |
| C8 | CH2 | CH2 | CHOAc | CHOH | CH2 | CH2 | CH2 | CHOH | CHOH | CHOAc | CH2 | CH2 | CHOAc |
| C9 | CH2 | CH2 | CH2 | CH2 | CH2 | CH2 | CH2 | CH | CH2 | CH2 | CH2 | CH2 | CH2 |
| C10 | CH | C | C | C | CE | CE | C | C | C | C | CE | CE | C |
| C11 | CH | C | C | C | C | C | C | C | C | C | C | C | CH |
| C12 | COL | COOH | COOH | COOH | COOH | COOH | COOH | COOH | COOH | COOH | COOH | COOH | COOH |
| C13 | CH3 | CH2(R) | CH2(R) | CH2(R) | CH2(R) | CH2(R) | CH2(R) | CH2(R) | CH2(R) | CH3(R) | CH2(R) | CH2(R) | CH3(R) |
| C14 | CH3 | CH2 | CH3 | CH3 | CH3 | CH3 | CH2 | CH3 | CH2 | CH3 | CH3 | CH3 | CH3 |
| C15 | CH3 | CH3 | CH3 | CH3 | CH3 | CH3 | CH3 | CH3 | CH3 | CH3 | CH3 | CH3 | CH3 |

| #carbon | Guaianolide | 14 | 15 | 16 | 17 | 18 | 19 | 20 | 21 | 22 | 23 | 24 | 25 |
|---|---|---|---|---|---|---|---|---|---|---|---|---|---|
| C1 | CH | CE | CH | CH | CH | CH | CE | CH | CH | CH | CH | C | C |
| C2 | CH2 | CH2 | CH2 | CH2 | CH2 | CH2 | CHE | CH2 | CH2 | CH2 | CH2 | CO | CO |
| C3 | CH2 | CH | CO | CH | CHE | CHE | CHE | CH2 | CH | CH | CHE | CH | CH |
| C4 | CH | C | C | C | CE | CE | CE | C | C | C | CE | C | C |
| C5 | CH | C | C | C | C | C | C | C | C | C | C | C | C |
| C6 | CHL | Cpp | Cpp | Cpp | Cpp | Cpp | Cpp | Cpp | Cpp | Cpp | Cpp | Cpp | Cpp |
| C7 | CH | CH | CH | CH | CH | CH | CH | CH | CH | CH | CH | CH | CH |
| C8 | CH2 | CHOH | CH2 | CHOAc | CHOAc | CHOH | CH2 | CHOAc | CHOH | CH2 | CHOH | CH2 | CH2 |
| C9 | CH2 | CH2 | CH2 | CH2 | CH2 | CH2 | CH2 | CH2 | CH2 | CH2 | CH2 | CH2 | CH2 |
| C10 | CH | CE | C | CE | CE | CE | CE | C | C | C | C | C | C |
| C11 | CH | CH | C | C | C | C | C | C | C | C | C | C | C |
| C12 | COL | COOH | COOH | COOH | COOH | COOH | COOH | COOH | COOH | COOH | COOH | COOH | COOH |
| C13 | CH3 | CH3(R) | CH2(R) | CH3(R) | CH3(R) | CH3(R) | CH2(R) | CH2(R) | CH2(R) | CH2(R) | CH2(R) | CH3(R) | CH3(R) |
| C14 | CH3 | CH2 | CH3 | CH2 | CH2 | CH2 | CH2 | CH3 | CH3 | CH3 | CH3 | CH3 | CH3 |
| C15 | CH3 | CH3 | CH3 | CH3 | CH3 | CH3 | CH3 | CH3 | CH3 | CH3 | CH3 | CH3 | CH3 |

Figure 1 (continued)

| #carbon | Gualanolide | 26 | 27 | 28 | 29 | 30 | 31 | 32 | 33 | 34 | 35 | 36 | 37 |
|---|---|---|---|---|---|---|---|---|---|---|---|---|---|
| C1 | CH | C | CH | C | COH | CH | CE | CH | CH | CH | CE | CE | C |
| C2 | CH2 | CO | CH2 | CO | CH2 | CH2 | CH2 | CO | COH | CO | CHE | CHE | CO |
| C3 | CH2 | CH | CO | CH | CH | CO | CH | CH | CH | CH | CHE | CHE | CH |
| C4 | CH | C | C | C | C | C | C | C | C | C | CE | CE | C |
| C5 | CH | CH | C | COH | CH | CH | CH | CH | CH | CH | CH | CH | CH |
| C6 | CHL | Cpp | Cpp | Cpp | Cpp | Cpp | Cpp | Cpp | Cpp | Cpp | Cpp | Cpp | Cpp |
| C7 | CH | CH | CH | CH | CH | CH | CH | CH | CH | CH | CH | CH | CH |
| C8 | CH2 | CHOAc | CH2 | CH2 | CH2 | CH2 | CH2 | CH2 | CHOH | CHOH | CHOH | CHOAc | CHOH |
| C9 | CH2 | CH2 | CH2 | CH2 | CH2 | CH2 | CH2 | CH2 | CH2 | CH2 | CH2 | CH2 | CH2 |
| C10 | CH | C | CH | C | COH | COH | CE | COH | C | COH | C | COH | C |
| C11 | CH | CH | COH | COH | COH | COH | CH | CH | CH | COH | COH | COH | CH |
| C12 | COL | COOH | COOH | COOH | COOH | COOH | COOH | COOH | COOH | COOH | COOH | COOH | COOH |
| C13 | CH3 | CH3(R) | CH2(R) | CH3(R) | CH3(R) | CH3(R) | CH3(R) | CH3(R) | CH3(R) | CH3(R) | CH2(R) | CH2(R) | CH3(R) |
| C14 | CH3 | CH3 | CH3 | CH3 | CH3 | CH3 | CH3 | CH3 | CH3 | CH3 | CH3 | CH3 | CH3 |
| C15 | CH3 | CH3 | CH3 | CH3 | CH3 | CH3 | CH3 | CH3 | CH3 | CH3 | CH3 | CH3 | CH3 |

| #carbon | Gualanolide | 38 | 39 | 40 | 41 | 42 | 43 | 44 | 45 | 46 | 47 | 48 | 49 |
|---|---|---|---|---|---|---|---|---|---|---|---|---|---|
| C1 | CH | CE | C | CE | CE | CH | CH | COH | CE | CH | CH | CH | CH |
| C2 | CH2 | CO | CO | CO | CH2 | CO | CH2 | CH2 | CHE | CO | CO | COH | COH |
| C3 | CH2 | CH | CH | CH | CH | CH | CHE | CH | CHE | CH2 | CH2 | CH2 | CH2 |
| C4 | CH | C | C | C | C | C | CE | C | CE | COH | COH | COH | COH |
| C5 | CH | CH | CH | CH | CH | CH | CH | CH | CH | CH | CH | CH | CH |
| C6 | CHL | Cpp | Cpp | Cpp | Cpp | Cpp | Cpp | Cpp | Cpp | Cpp | Cpp | Cpp | Cpp |
| C7 | CH | CH | CH | CH | CH | CH | CH | CH | CH | CH | CH | CH | CH |
| C8 | CH2 | CH2 | CHOH | CHOH | CH2 | CHOH | CH2 | CHOAc | CHOAc | CH2 | CH2 | CH2 | CH2 |
| C9 | CH2 | CH2 | CH2 | CH2 | CH2 | CH2 | CH2 | CH2 | CH2 | COH | COH | COH | COH |
| C10 | CE | CE | C | CE | CE | C | CE | C | CE | CH | CH | CH | CH |
| C11 | CH | CH | CH | CH | CH | CH | CH | CH | CH | CH | CH | CH | CH |
| C12 | COL | COOH | COOH | COOH | COOH | COOH | COOH | COOH | COOH | COOH | COOH | COOH | COOH |
| C13 | CH3 | CH3(R) | CH3(R) | CH3(R) | CH3(R) | CH2(R) | CH3(R) | CH2(R) | CH3(R) | CH3(R) | CH3(R) | CH3(R) | CH3(R) |
| C14 | CH3 | CH3 | CH3 | CH3 | CH3 | CH3 | CH3 | CH3 | CH3 | CH3 | CH3 | CH3 | CH3 |
| C15 | CH3 | CH3 | CH3 | CH3 | CH3 | CH3 | CH3 | CH3 | CH3 | CH3 | CH3 | CH3 | CH3 |

Figure 1 (continued)

| #carbon | Guaianolide | 50 | 51 | * | 52 | 53 | 54 | 55 | 56 | 57 | 58 | 59 | 60 |
|---|---|---|---|---|---|---|---|---|---|---|---|---|---|
| C1 | CH | C | C | CH2 | CHOH | CH2 | CH2 | CHOH | CH | CH2 | CH2 | CH | CH |
| C2 | CH2 | CH | CH | CH2 | CH2 | CH2 | CH2 | CH2 | CH | CH2 | CH2 | CH | CH |
| C3 | CH2 | CH2 | CH2 | CH2 | CHOH | CH2 | CH2 | CO | CO | CHOH | CO | CO | CO |
| C4 | CH | COH | C | CH | C | COH | C | CH | C | CHOH | CH | C | C |
| C5 | CH | CH | CH | CH | C | CH | C | CH | CH | CH | CH | C | C |
| C6 | CHL | Cpp | Cpp | CHL | Cpp | Cpp | Cpp | Cpp | Cpp | Cpp | Cpp | Cpp | Cpp |
| C7 | CH | CH | CH | CH | CH | CH | CH | CH | CH | CH | C | CH | CH |
| C8 | CH2 | CHOAc | CH2 | CH2 | CH2 | CH2 | CH2 | CH2 | CHOH | CH | CH | CH2 | CH2 |
| C9 | CH2 | CH | CH2 | CH2 | CH2 | CH2 | CH2 | CH2 | CH2 | CH | CH2 | CH2 | CH2 |
| C10 | CH | C | C | C | C | C | C | C | C | C | C | C | C |
| C11 | CH | CH | CH | CH | C | C | C | C | CH | C | CH | CH | CH |
| C12 | COL | COOH | COOH | COL | COOH | COOH | COOH | COOH | COOH | COOH | COOH | COOH | COOH |
| C13 | CH3 | CH3(R) | CH3(R) | CH3 | CH3 | CH3 | CH2(R) | CH2(R) | CH3(R) | CH3(R) | CH3(R) | CH3(R) | CH3(R) |
| C14 | CH3 | CH3 | CH3 | CH3 | CH3 | CH3 | CH3 | CH3 | CH3 | CH3 | CH3 | CH3 | CH3 |
| C15 | CH3 | CH3 | CH3 | CH3 | CH3 | CH3 | CH3 | CH3 | CH3 | CH3 | CH3 | CH3 | CH3 |

\# = Eudesmanolide

| #carbon | Eudesmanolide | 61 | 62 | 63 | 64 | 65 | 66 | 67 | 68 | 69 | 70 | 71 | 72 |
|---|---|---|---|---|---|---|---|---|---|---|---|---|---|
| C1 | CH2 | CO | CH2 | CH2 | CH2 | CH2 | CHOH | CH2 | CHOH | CHOH | CHOH | CHOH | CO |
| C2 | CH2 | CH2 | CH2 | CH2 | CH2 | CH2 | CH2 | CH2 | CH2 | CH2 | CH2 | CH2 | CH2 |
| C3 | CH2 | CH2 | CO | CO | CH2 | CH2 | CHOH | CHOH | CH2 | CH2 | CHOH | CH2 | CH2 |
| C4 | CH | C | C | CH | C | COH | C | CH | C | C | C | C | C |
| C5 | CH | C | C | CH | CH | CH | CH | CH | CH | CH | CH | CH | CH |
| C6 | CHL | Cpp | Cpp | Cpp | Cpp | Cpp | Cpp | Cpp | Cpp | Cpp | Cpp | Cpp | Cpp |
| C7 | CH | CH | CH | CH | CH | C | CH | CH | CH | CH | CH | CH | CH |
| C8 | CH2 | CHOH | CH2 | CH2 | CH2 | CH2 | CH2 | CH2 | CH2 | CH2 | CHOH | CH2 | CH2 |
| C9 | CH2 | CH2 | CH2 | CH2 | CH2 | CH2 | CH2 | CH2 | CH2 | CH2 | CH2 | CH2 | CH2 |
| C10 | C | C | C | C | C | C | C | C | C | C | C | C | C |
| C11 | CH | CH | CH | CH | CH | CH | C | C | C | C | CH | CH | CH |
| C12 | COL | COOH | COOH | COOH | COOH | COOH | COOH | COOH | COOH | COOH | COOH | COOH | COOH |
| C13 | CH3 | CH3(R) | CH3(R) | CH3(R) | CH2(R) | CH2OH | CH3(R) | CH3(R) | CH3(R) | CH3(R) | CH2(R) | CH3(R) | CH3(R) |
| C14 | CH3 | CH3 | CH3 | CH3 | CH3 | CH3 | CH3 | CH3 | CH3 | CH3 | CH3 | CH3 | CH3 |
| C15 | CH3 | CH3 | CH2 | CH3 | CH2 | CH3 | CH3 | CH3 | CH2 | CH2 | CH2 | CH2 | CH3 |

Figure 1 (continued)

| #carbon | Eudesmanolide | 73 | 74 | 75 | 76 | 77 | 78 | 79 | 80 | 81 | 82 | 83 | 84 |
|---|---|---|---|---|---|---|---|---|---|---|---|---|---|
| C1 | CH2 | COH | CO | CO | CHOH | CHOH | CHOH | CHOH | CHOH | CHOH | CHOH | CO | C |
| C2 | CH2 | CH2 | CH2 | CH2 | CH2 | CH2 | CH2 | CH2 | CH2 | CH2 | CH2 | CH2 | CO |
| C3 | CH2 | CH2 | CH2 | CH2 | CO | CH2 | CH2 | CO | CO | CH2 | CH2 | CH2 | CH |
| C4 | CH | C | C | CE | C | C | C | CH | CH | C | C | C | CH |
| C5 | CH | C | C | CE | C | COH | C | CH | CH | COH | C | C | C |
| C6 | CHL | Cpp | Cpp | Cpp | Cpp | Cpp | Cpp | Cpp | Cpp | Cpp | Cpp | Cpp | Cpp |
| C7 | CH | CH | CH | CH | CH | CH | CH | CH | CH | CH | CH | CH | CH |
| C8 | CH2 | CHOAc | CH2 | CH2 | CH2 | CH2 | CH2 | CH2 | CH2 | CH2 | CH2 | CH2 | CH2 |
| C9 | CH2 | CH2 | CH2 | CH2 | CH2 | CH2 | CH2 | CH2 | CH2 | CH2 | CH2 | CH2 | CH2 |
| C10 | C | C | C | C | C | C | C | C | C | C | C | C | C |
| C11 | CH | CH | CH | CH | CH | CH | CH | CH | CH | CH | CH | CH | CH |
| C12 | COL | COOH | COOH | COOH | COOH | COOH | COOH | COOH | COOH | COOH | COOH | COOH | COOH |
| C13 | CH3 | CH3(R) | CH3(R) | CH3(R) | CH3(R) | CH3(R) | CH3(R) | CH3(R) | CH3(R) | CH3(R) | CH2(R) | CH3(R) | CH3(R) |
| C14 | CH3 | CH3 | CH3 | CH3 | CH3 | CH3 | CH3 | CH3 | CH3 | CH3 | CH3 | CH3 | CH3 |
| C15 | CH3 | CH3 | CH3 | CH3 | CH2 | CH2 | CH3 | CH3 | CH3 | CH2 | CH3 | CH3 | |

| #carbon | Eudesmanolide | 85 | 86 | 87 | 88 | 89 | 90 | 91 | 92 | 93 | 94 | 95 | 96 |
|---|---|---|---|---|---|---|---|---|---|---|---|---|---|
| C1 | CH2 | CHOH | CH2 | CH2 | CO | CO | CHOAc | CHOH | CHOH | CHOH | CO | CH2 | CO |
| C2 | CH2 | CH2 | CH2 | CH2 | CH | CH | CH2 | CH2 | CH2 | CH2 | CH | CH2 | CH2 |
| C3 | CH2 | CHOH | CH2 | CHOH | CH | CH | CHOAc | CO | CH | CH | CHOH | CO | CH2 |
| C4 | CH | C | C | C | C | C | C | C | C | C | CHOH | CH | COH |
| C5 | CH | CH | CH | COH | COH | C | C | CH | CH | CH | CH | CH | CH |
| C6 | CHL | Cpp | Cpp | Cpp | Cpp | Cpp | Cpp | Cpp | Cpp | Cpp | Cpp | Cpp | Cpp |
| C7 | CH | CH | CH | CH | CH | CH | CH | CH | CH | CH | CH | CH | CH |
| C8 | CH2 | CH2 | CH2 | CHOH | CH2 | CH2 | CH2 | CH2 | CH2 | CHOAc | CH2 | CHOH | CH2 |
| C9 | CH2 | CH2 | CH2 | CH2 | CH2 | CH2 | CH2 | CH2 | CH2 | CH2 | CH2 | CH2 | CH2 |
| C10 | C | C | C | C | C | C | C | C | C | C | C | C | C |
| C11 | CH | CH | CH | CH | CH | CH | CH | CH | CH | CH | CH | CH | CH |
| C12 | COL | COOH | COOH | COOH | COOH | COOH | COOH | COOH | COOH | COOH | COOH | COOH | COOH |
| C13 | CH3 | CH2(R) | CH2(R) | CH2(R) | CH2(R) | CH2(R) | CH2(R) | CH2(R) | CH2(R) | CH2(R) | CH2(R) | CH3(R) | CH3(R) |
| C14 | CH3 | CH3 | CH3 | CH3 | CH3 | CH3 | CH3 | CH3 | CH3 | CH3 | CH3 | CH3 | CH3 |
| C15 | CH3 | CH2 | CH3 | CH3 | CH3 | CH3 | CH3 | CH3 | CH3 | CH3 | CH3 | CH3 | CH3 |

Figure 1 (continued)

| #carbon | Eudesmanolide | 97 | 98 | 99 | ## | 100 | 101 | 102 | 103 | 104 | 105 | 106 | 107 |
|---|---|---|---|---|---|---|---|---|---|---|---|---|---|
| C1 | CH2 | CHOH | CHOH | CHOH | CH2 | CH | CH | CH | CH | CH | CH | CH | CH |
| C2 | CH2 | CH2 | CH2 | CH2 | CH2 | CH2 | CH2 | CH2 | CH2 | CH2 | CH2 | CH2 | CH2 |
| C3 | CH2 | CHE | CHOH | CO | CH2 | CHOH | CO | CO | CHOH | CH2 | CH2 | CH2 | CH2 |
| C4 | CH | CE | C | C | CH | C | CH | CH | CH | C | C | C | C |
| C5 | CH | CH | CH | CH | CH | CH | CH | CH | CH | CH | CH | CH | CH |
| C6 | CHL | Cpp | Cpp | Cpp | CHL | Cpp | Cpp | Cpp | Cpp | Cpp | Cpp | Cpp | Cpp |
| C7 | CH | CH | CH | CH | CH | CH | CH | CH | CH | CH | CH | CH | CH |
| C8 | CH2 | CH2 | CH2 | CH2 | CH2 | CH2 | CH2 | CH2 | CH2 | CHOH | CHOH | CHOH | CH2 |
| C9 | CH2 | CH2 | CH2 | CH2 | CH2 | CH2 | CH2 | CH2 | CH2 | CH2 | CH2 | CH2 | CHOAc |
| C10 | C | C | C | C | C | C | C | C | C | C | C | C | C |
| C11 | CH | CH | CH | CH | CH | CH | CH | CH | CH | CH | CH | CH | CH |
| C12 | COL | COOH | COOH | COOH | COL | COOH | COOH | COOH | COOH | COOH | COOH | COOH | COOH |
| C13 | CH3 | CH2(R) | CH2(R) | CH2(R) | CH3 | CH3(R) | CH3(R) | CH3(R) | CH3(R) | CH3(R) | CH3(R) | CH3(R) | CH3(R) |
| C14 | CH3 | CH3 | CH3 | CH3 | CH3 | CH3 | CH3 | CH3 | CH3 | CH3 | CH3 | CH3 | CH3 |
| C15 | CH3 | CH3 | CH3 | CH3 | CH3 | CH3 | CH3 | CH3 | CH3 | CH3 | CH3 | CH3 | CH3 |

## = Germacranolide

| #carbon | Germacranolide | 108 | 109 | 110 | 111 | 112 | 113 | 114 | 115 | 116 | 117 | 118 | 119 |
|---|---|---|---|---|---|---|---|---|---|---|---|---|---|
| C1 | CH2 | CHE | CH | CHOH | CHOH | CH | CH2 | CHOH | CHOH | CHOH | CHOH | CH | CO |
| C2 | CH2 | CH2 | CH2 | CH2 | CH2 | CH2 | CH2 | CHOH | CH2 | CH2 | CHOH | CH2 | CH2 |
| C3 | CH2 | CH2 | CH2 | CH2 | CH2 | CHOAc | CHOH | CHOH | CHOH | CHOH | CH2 | CH2 | CH2 |
| C4 | CH | C | CE | C | C | C | C | C | C | C | C | C | C |
| C5 | CH2 | CH | CHE | CH | C | CH | C | C | C | C | C | CH | CH |
| C6 | CHL | Cpp | Cpp | Cpp | Cpp | Cpp | Cpp | Cpp | Cpp | Cpp | Cpp | Cpp | Cpp |
| C7 | CH | CH | CH | CH | CH | CH | CH | CH | CH | CH | CH | CH | CH |
| C8 | CH2 | CH2 | CH2 | CH2 | CH2 | CH2 | CHOH | CH2 | CH2 | CH2 | CH2 | CH2 | CH2 |
| C9 | CH2 | CHOAc | CHOAc | CH2 | CH2 | CH2 | CH2 | CH2 | CH2 | CH2 | CH2 | CHOAc | CH2 |
| C10 | CH | CE | CE | C | C | C | C | C | C | C | C | C | C |
| C11 | CH | CH | CH | CH | CH | CH | CH | CH | CH | CH | CH | CH | CH |
| C12 | COL | COOH | COOH | COOH | COOH | COOH | COOH | COOH | COOH | COOH | COOH | COOH | COOH |
| C13 | CH3 | CH3(R) | CH3(R) | CH2(R) | CH3(R) | CH2(R) | CH2(R) | CH2(R) | CH3(R) | CH2(R) | CH2(R) | CH3(R) | CH2(R) |
| C14 | CH3 | CH3 | CH3 | CH3 | CH2 | CH3 | CH2 | CH2 | CH2 | CH2 | CH2 | CH2 | CH2 |
| C15 | CH3 | CH3 | CH3 | CH3 | CH3 | CH3 | CH3 | CH3 | CH3 | CH3 | CH3 | CH3 | CH3 |

Figure 1 (continued)

| #carbon | Germacranolide | 120 | 121 | 122 | 123 | 124 | 125 | 126 | 127 | 128 | 129 | 130 | 131 |
|---|---|---|---|---|---|---|---|---|---|---|---|---|---|
| C1 | CH2 | CHOH | CH | CH | CH | CHOH | CH2 | CH2 | CH2 | CH2 | CHOH | CH2 | CH2 |
| C2 | CH2 | CH2 | CH2 | CH2 | CH2 | CH2 | CH2 | CH2 | CH2 | CH2 | CH2 | CH2 | CH2 |
| C3 | CH2 | CH2 | CH2 | CHOH | CHOH | CH2 | CHOH | CHOH | CO | CO | CH2 | CO | CHOH |
| C4 | CH | C | C | C | C | C | C | C | C | C | C | C | C |
| C5 | CH2 | CH | CH | CH | CH | CH | CH | CH2 | CH2 | CH2 | CH | CH2 | CH2 |
| C6 | CHL | Cpp | Cpp | Cpp | Cpp | Cpp | Cpp | Cpp | Cpp | Cpp | Cpp | Cpp | Cpp |
| C7 | CH | CH | CH | CH | CH | CH | CH | CH | CH | CH | CH | CH | CH |
| C8 | CH2 | CH2 | CH2 | CH2 | CH2 | CHOH | CHOH | CHOH | CHOH | CHOH | CH2 | CHOH | CHOH |
| C9 | CH2 | CH2 | CH2 | CH2 | CH2 | CH2 | CH | CH | CH | CH2 | CH | CH | CH |
| C10 | CH | C | C | C | C | C | C | C | C | C | C | C | C |
| C11 | CH | CH | C | CH | CH | CH | CH | CH | CH | CH | CH | CH | CH |
| C12 | COL | COOH | COOH | COOH | COOH | COOH | COOH | COOH | COOH | COOH | COOH | COOH | COOH |
| C13 | CH3 | CH3(R) | CH2(R) | CH3 | CH3 | CH2(R) | CH2(R) | CH2(R) | CH2(R) | CH2(R) | CH3(R) | CH3(R) | CH3(R) |
| C14 | CH3 | CH2 | CH3 | CH3 | CH2 | CH2 | CH3 | CH2 | CH3 | CH2 | CH3 | CH3 | CH3 |
| C15 | CH3 | CH3 | CH3 | CH3 | CH3 | CH3 | CH3 | CH3 | CH3 | CH3 | CH3 | CH2 | CH2 |

| #carbon | Germacranolide | 132 | 133 | 134 | 135 | 136 | 137 | 138 | 139 | 140 | 141 |
|---|---|---|---|---|---|---|---|---|---|---|---|
| C1 | CH2 | CH | CH | CH | CHE | CH | CH | CHE | CH | CH | CHE |
| C2 | CH2 | CH2 | CH2 | CH2 | CH2 | CH2 | CH2 | CH2 | CH2 | CH2 | CH2 |
| C3 | CH2 | CH2 | CH2 | CH2 | CE | C | CE | COH | C | C | CH2 |
| C4 | CH | C | C | CE | CHE | C | CHE | CHE | C | C | CH |
| C5 | CH2 | CH | CH | CHE | CHL | CHOH | CHOH | CHOH | CH | CH | CH2 |
| C6 | CHL | Cpp | Cpp | Cpp | CH2 | Cpp | CH | CH | Cpp | Cpp | Cpp |
| C7 | CH | CH | CH | CH | CH2 | CH | CH | CH | CH2 | CH | CH2 |
| C8 | CH2 | CHOAc | CHOH | CHOAc | CE | CH2 | CH2 | Cpp | CH2 | CH2 | CE |
| C9 | CH2 | CH2 | CH2 | CH2 | C | C | C | C | C | C | C |
| C10 | CH | C | C | C | COOH | COOH | COOH | COOH | COOH | COOH | COOH |
| C11 | CH | COOH | COOH | COOH | CH2(R) | CH2(R) | CH2(R) | CH2 | CH2(R) | CH2(R) | CH2(R) |
| C12 | COL | CH2(R) | CH3 | CH3 | CH3 | CH3 | CH3 | CH2 | CH3 | CH3 | CH3 |
| C13 | CH3 | CH3 | CH3 | CH3 | CH3 | CH3 | CH3 | CH3 | CH3 | CH3 | CH3 |
| C14 | CH3 | CH3 | | | | | | | | | |
| C15 | CH3 | | | | | | | | | | |

Figure 1 (continued)

| #carbon | Eudesmanolide | 142 | 143 | 144 | 145 | 146 | 147 | 148 | 149 | 150 |
|---|---|---|---|---|---|---|---|---|---|---|
| C1 | CH2 | CH | CH2 | CH2 | CHOH | CHOH | CH2 | CHOH | CHOH | CH2 |
| C2 | CH2 | CH | CH2 | CH2 | CH2 | CH2 | CH2 | CH2 | CH2 | CH2 |
| C3 | CH2 | CO | CH2 | CH2 | CHOH | CHOH | CH2 | CH2 | CH2 | CH2 |
| C4 | CH | C | C | C | C | C | C | C | C | C |
| C5 | CH | C | CCOOH | CCOOH | CH | CH | C | C | C | C |
| C6 | CHL | CH2 | CH2 | CH2 | CH2 | CH2 | CH2 | CH | CH2 | CH |
| C7 | CH | CH | CH | CH | CH | CH | CH | CH | CH | C |
| C8 | CH2 | Cpp | Cpp | Cpp | Cpp | Cpp | Cpp | Cpp | Cpp | Cpp |
| C9 | CH2 | CH2 | CH2 | CH2 | CH2 | CH2 | CH2 | CH2 | CH2 | CH2 |
| C10 | C | C | C | C | C | C | C | C | C | C |
| C11 | CH | C | C | C | CH | C | C | C | C | C |
| C12 | COL | COOH | COOH | COOH | COL | COOH | COOH | COOH | COOH | COOH |
| C13 | CH3 | CH2(R) | CH2(R) | CH2(R) | CH3(R) | CH2(R) | CH2(R) | CH2(R) | CH2(R) | CH3(R) |
| C14 | CH3 | CH3 | CH3 | CH3 | CH3 | CH3 | CH3 | CH3 | CH3 | CH3 |
| C15 | CH3 | CH3 | CH3 | CH3 | CH2 | CH2 | CH3 | CH3 | CH2 | CH2 |

Figure 1 (continued)

| #carbon | Guaianolide | Estafiatine derivative | Estafiatine | Grosshemin derivative | Grosshemin | Grosshemin acetate derivative | Arglabin derivative | Arglabin | Inuchinenolide C derivative | Inuchinenolide C |
|---|---|---|---|---|---|---|---|---|---|---|
| C1 | CH | CH | CH | CH | CH | CH | CE | CE | CH | CH |
| C2 | CH2 | CH2 | CH2 | CH2 | CH2 | CH2 | CH2 | CH2 | CHOAc | CHOAc |
| C3 | CH2 | CHE | CHE | CO | CO | CO | CH | CH | CH2 | CH2 |
| C4 | CH | CE | CE | CH | CH | CH | C | C | CHOAc | CHOAc |
| C5 | CH | CH | CH | CH | CH | CH | CH | CH | C | C |
| C6 | CHL | Cpp | CL | Cpp | CL | Cpp | Cpp | CL | CHOH | CHOH |
| C7 | CH | CH | CH | CH | CH | CH | CH | CH | CH | CH |
| C8 | CH2 | CH2 | CH2 | CHOH | CHOH | CHOAc | CH2 | CH2 | Cpp | CL |
| C9 | CH2 | CH2 | CH2 | CH2 | CH2 | CH2 | CH2 | CH2 | CH2 | CH2 |
| C10 | CH | C | C | C | C | C | CE | CE | CH | CH |
| C11 | CH | CH | CH | CH | CH | CH | C | C | C | C |
| C12 | COL | COOH | COL | COOH | COL | COOH | COOH | COL | COOH | COL |
| C13 | CH3 | CH2(R) | CH2 | CH2(R) | CH2 | CH2(R) | CH2(R) | CH2 | CH2(R) | CH2 |
| C14 | CH3 | CH3 | CH3 | CH3 | CH3 | CH3 | CH3 | CH3 | CH3 | CH3 |
| C15 | CH3 | CH3 | CH3 | CH3 | CH3 | CH3 | CH3 | CH3 | CH3 | CH3 |

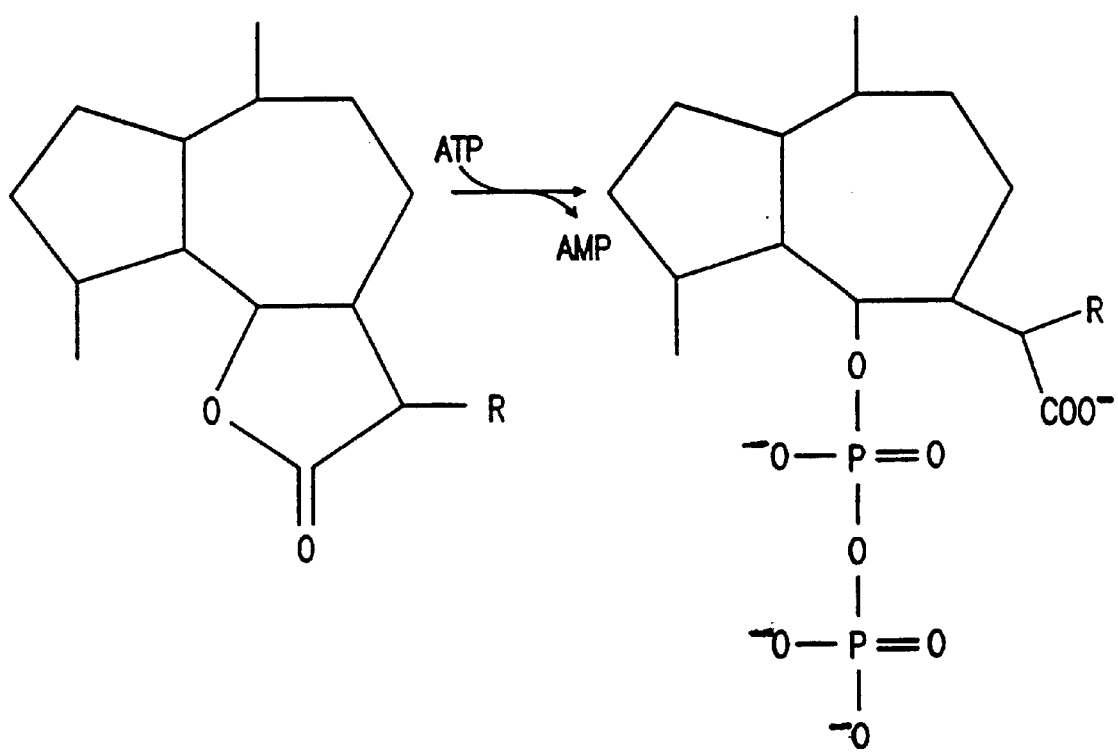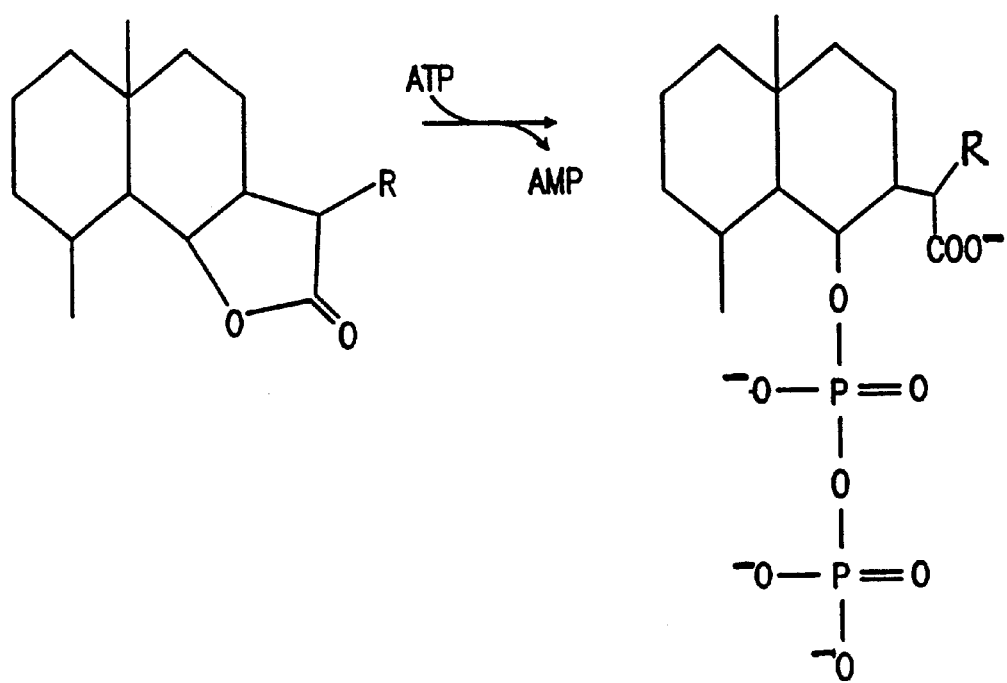
Figure 2

Receptor Selection and Amplification Technology of Ras-NIH3T3 Cells

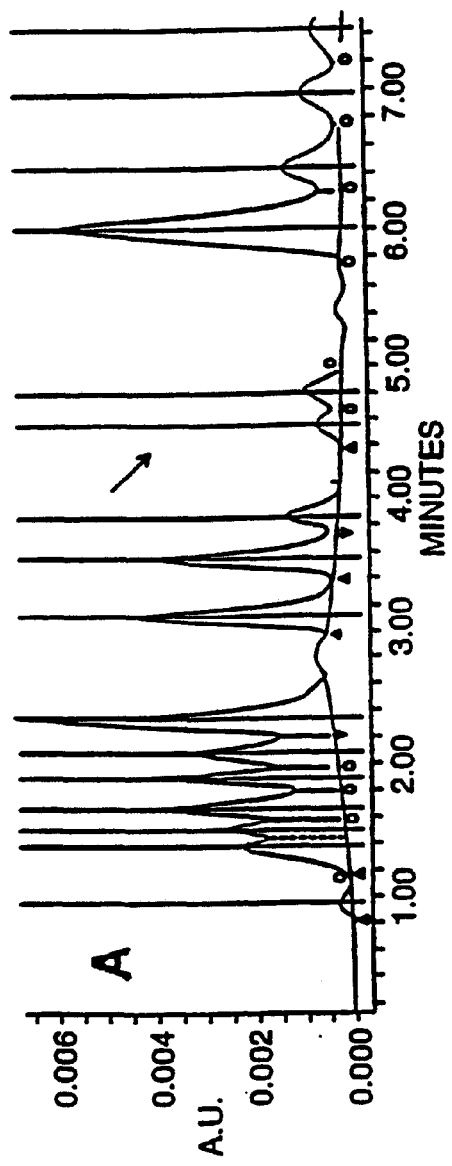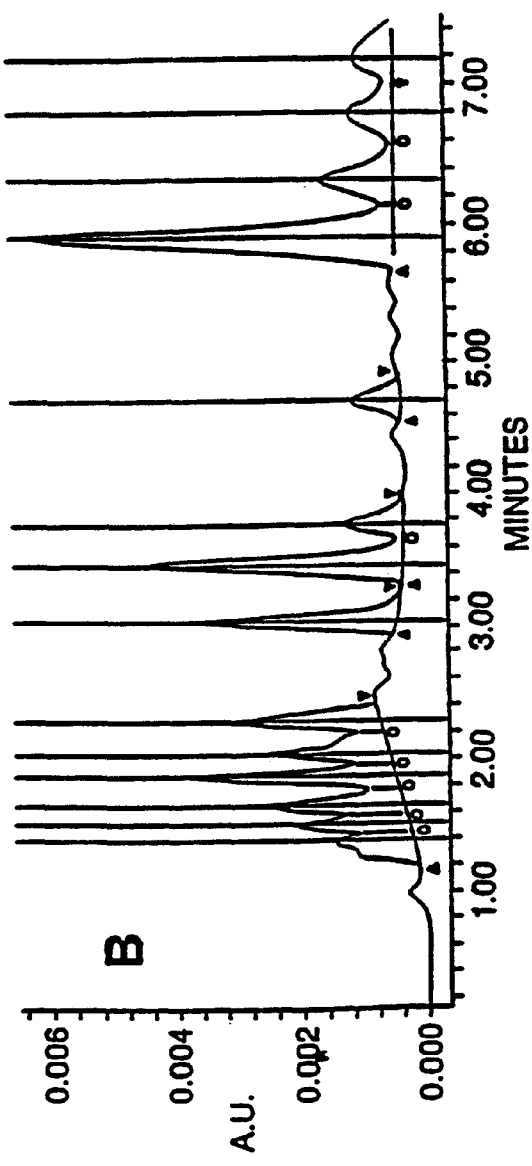
Figure 4

ATP Bioluminescence Assay

ATP Bioluminescence Assay

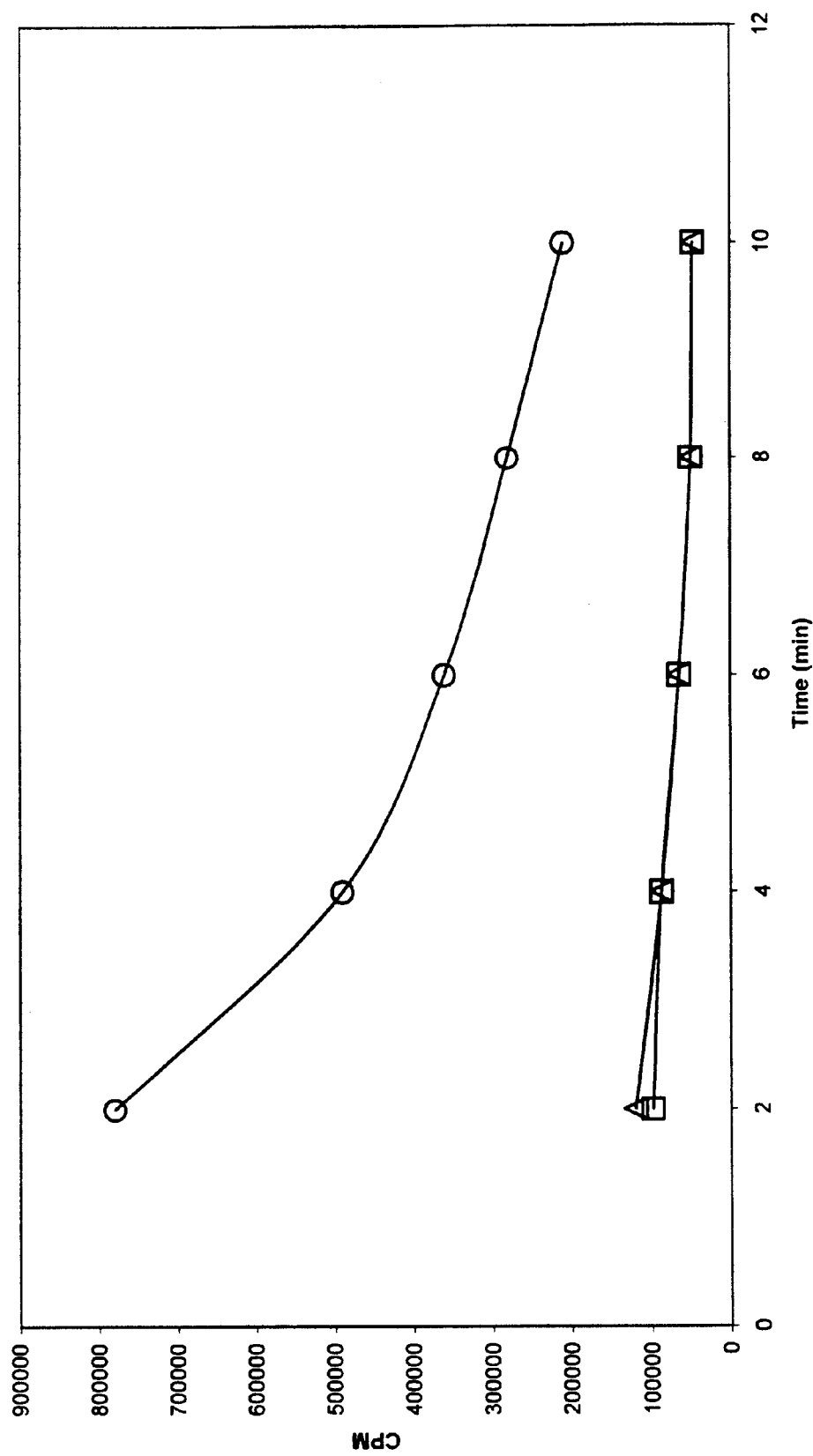

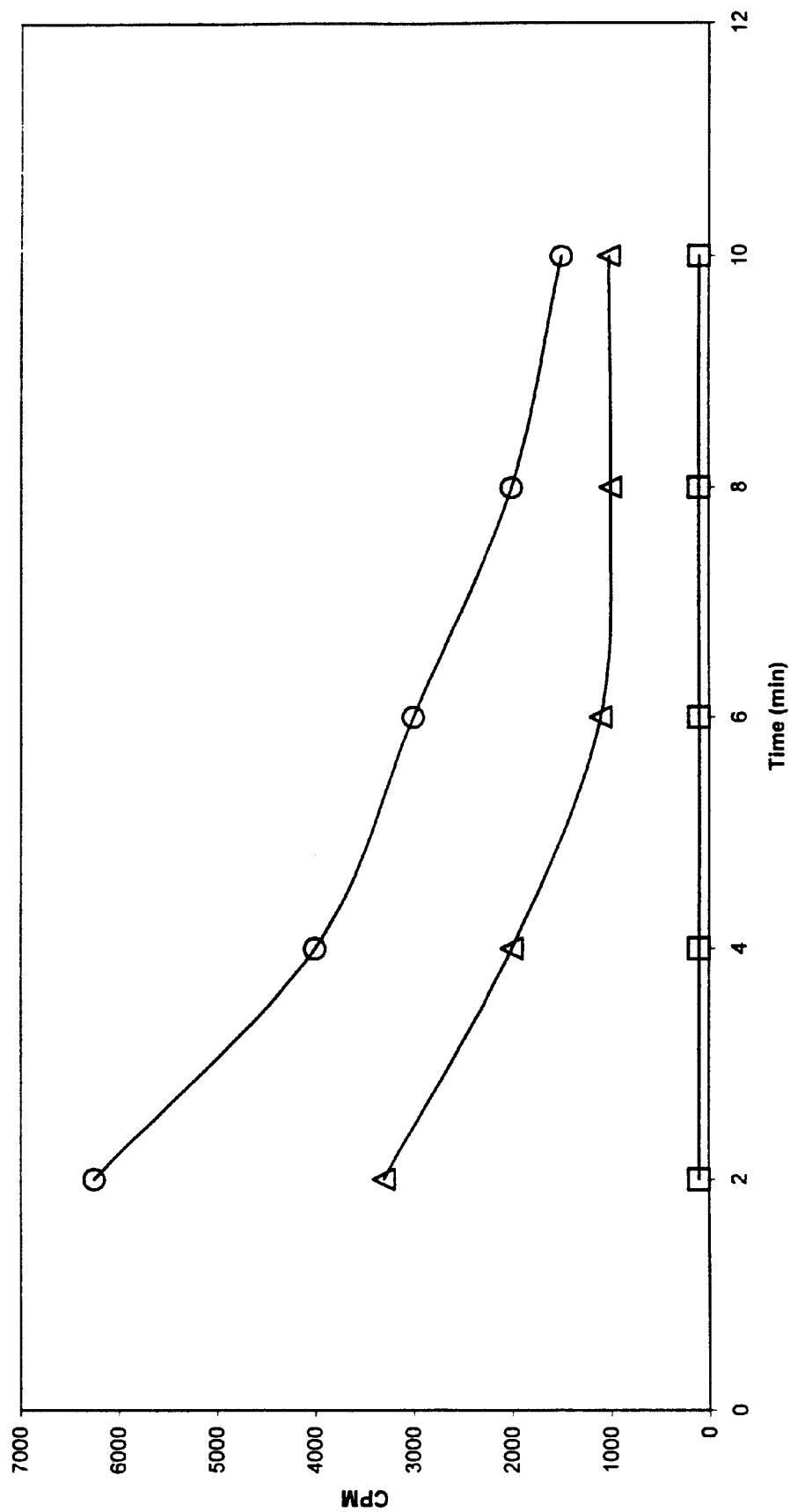

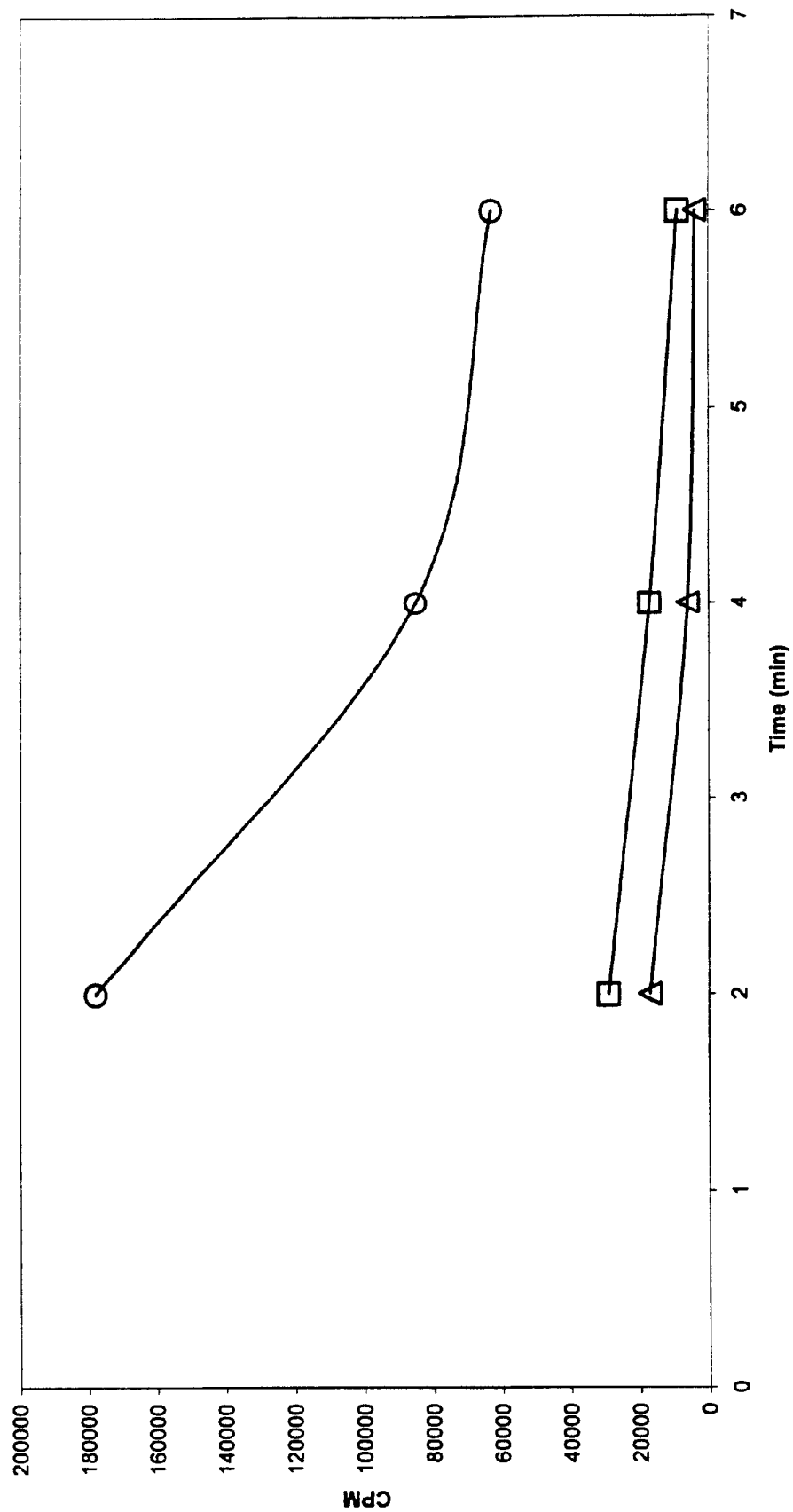

FARNESYL-PROTEIN TRANSFERASE INHIBITORS

CROSS REFERENCE TO RELATED APPLICATIONS

This application is a division of application No. 09/030,300 filed Feb. 25, 1998 now U.S. Pat. No. 6,051,565 which is a continuation-in-part of application No. 08/934,229 filed Sep. 19, 1997 now U.S. Pat. No. 5,902,809 and application No. 08/934,228 filed on Sep. 19, 1997 and application No. 08/934,471 filed on Sep. 19, 1997 and claims priority from U.S. Provisional application No. 60/051,681, filed on Jul. 3, 1997, claimed under 35 U.S.C. §119.

BACKGROUND OF THE INVENTION

The invention relates to farnesyl-protein transferase inhibitors.

Ras proteins transduce extracellular signals to the nucleus and are part of a large superfamily of GTP-binding proteins that are active when bound to GTP and inactive when bound to GDP. After stimulation by receptor activation, Ras protein binds GTP and transmits a proliferative signal to the nucleus. Hydrolysis of GTP to GDP by a GTPase returns Ras to an inactive state. There are three human ras genes, Harvey (H), Kirsten (K) and N-ras, that each encode a 21 kDa Ras protein. Two splice variants of K-ras, K-4A and K4B, also exist. Approximately 30% of all human cancers harbor ras mutations that typically impair GTP-ase activity, rendering Ras protein locked in a GTP-bound or active state. Kelloff, G. J. et al., (1997), *Cancer Epidemiol. Biomarkers Prev.*, 6(4):267–282.

Ras proteins are initially synthesized as cytoplasmic, soluble proteins. Post-translational modifications serve to attach Ras protein to the plasma membrane. The amino acid sequences of Ras proteins all end in CAAX, where C is cysteine, A is an aliphatic amino acid and X is another amino acid. The first post-translational modification of Ras protein is attachment of a lipophilic 15-carbon farnesyl moiety (farnesyl pyrophosphate, FPP) to the cysteine residue of the CAAX moiety through a farnesyl-protein transferase (FPT) catalyzed reaction. Subsequently, the AAX tripeptide is proteolytically cleaved and the farnesylated cysteine is converted to its methyl ester. Additional lipid modifications of upstream residues further stabilize the association of Ras protein with the plasma membrane. Lerner, E. C. et al., (1997), *Anticancer Drug Des.*, 12:229–238. A related enzyme, geranylgeranyltransferase (GGT) can transfer a 20-carbon geranylgeranyl moiety to the cysteine residue of the CAAX moiety when X is leucine.

It has been shown that inhibition of FPT blocks the anchorage-independent growth of fibroblasts transformed with ras mutants and results in other morphological changes and downi-regulation of Ras-protein activated signalling cascades. Omer, Ch. A. et al., (1997), *BioFactors*, 6:359–366.

A number of farnesylation inhibitors have been developed. One class of inhibitors includes FPP competitive inhibitors that bind to FPT at the FPP binding site. Compounds of this group include synthetic analogs of FPP such as (α-hydroxyfarnesyl)phosphonic acid, amide analogs, hydroxamate analogs, pivolyloxymethyl ester analogs and difluorinated β-ketophosphonic acid, as well as natural products such as actinoplanic acids, chaetomellic acids, manumycin, perillyl alcohol, d-limonene and metabolites, RPR113228 and zaragozic acid. Many of these compounds are selective for GGT rather than FPT and are inactive in whole cells. Perillyl alcohol and d-limonene have chemopreventive activity and reduce tumor size in animals.

A second class of inhibitors includes CAAX tetrapeptides that can serve as substrates and/or competitive inhibitors of FPT. Structure activity analysis has indicated that nonfarnesylated tetrapeptides containing an aromatic amino acid at the $A_2$ position of $CA_1A_2X$ and a positive charge on the cysteine amino group are the most potent. Tetrapeptides have limited use in vivo since they are inactive in whole cells. A variety of peptidomimetics that are highly selective for FPT and are potent FPT inhibitors have also been synthesized. In most of these compounds, the peptide backbone was modified to increase stability. To increase membrane penetration, the C-terminal carboxylate was masked in certain compounds using an ester prodrug strategy. Many of these compounds inhibit H-Ras processing in cells and also suppress growth of tumors in animals. For a review of peptidomimetics, see Qian, Y. et al., (1997), *Biopolymers*, 43:2541.

There are additional FPT inhibitors including barceloneic acid, cylindrol A, fusidienol, patulin, preussomerins and streptonigrins that have been identified from natural products. The mechanism of action of these compounds is unknown. Kelloff, G. J. et al, 1997, supra.

SUMMARY OF THE INVENTION

The invention provides novel phosphosesquiterpenes that function as farnesyl-protein transferase inhibitors. The phosphorylated compounds can be used as effective chemotherapeutic agents with fewer side effects than typically follow from use of other chemotherapeutic agents.

In one aspect, the invention features a substantially pure preparation of a phosphosesquiterpene. The phosphosesquiterpene is a phosphorylation product of a sesquiterpene lactone selected from the group consisting of ambrosanolides, psilostachyanolides, cadinanolides, eremanolides, xanthanolides, guaianolides, germacranolides, elamanolides and eudesmanolides.

The phosphosesquiterpene can be a phosphorylation product of the sesquiterpene lactone having formula A.

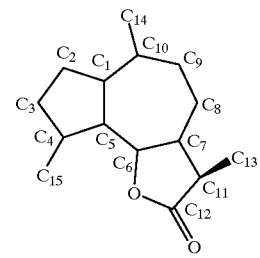

In formula A, $C_1$ is further bonded to hydrogen, hydroxy, short chain alkanoyloxy, or $C_2$ or $C_{10}$ via a double bond or an oxy linkage. $C_2$ is further bonded to at least one of the following substituents independently selected from the group consisting of hydrogen, hydroxy, oxo, short chain allanoyloxy, and $C_1$ or $C_3$ via a double bond or an oxy linkage. $C_3$ is further bonded to at least one of the following substituents independently selected from the group consisting of hydrogen, oxo, and $C_2$ or $C_4$ via a double bond or an oxy linkage. $C_4$ is further bonded to hydrogen, hydroxy, short chain alkanoyloxy, or $C_3$, $C_5$, or $C_{15}$ via an oxy linkage or a double bond. $C_5$ is further bonded to hydrogen, hydroxy, short chain alkanoyloxy, or $C_4$ via an oxy linkage or a double bond. $C_6$ is further bonded to hydrogen and $C_7$ is further bonded to hydrogen or $C_{11}$ via a double bond. $C_8$ is further bonded to at least one of the following substituents independently selected from the group consisting of hydrogen, hydroxy, and short chain alkanoyloxy. $C_9$ is further bonded to at least one of the following substituents independently selected from the group consisting of hydrogen, and $C_{10}$ via a double bond. $C_{10}$ is further bonded to hydrogen, hydroxy, short chain alkanoyloxy, $C_1$ or $C_{14}$ via an oxy linkage, or $C_1$, $C_9$, or $C_{14}$ via a double bond. $C_{11}$ is further bonded to hydrogen, hydroxy, hydroxymethyl, or $C_7$ or $C_{13}$ via a double bond. $C_{13}$ is further bonded to at least one of the following substituents independently selected from the group consisting of hydrogen, an optionally substituted alkylamino salt, and $C_{11}$ via a double bond. $C_{14}$ is further bonded to at least one of the following substituents independently selected from the group consisting of hydrogen and $C_{10}$ via an oxy linkage or a double bond. $C_{15}$ is further bonded to at least one of the following substituents independently selected from the group consisting of hydrogen and $C_4$ via an oxy linkage or a double bond.

The phosphosesquiterpene can be a phosphorylation product of the sesquiterpene lactone having formula B.

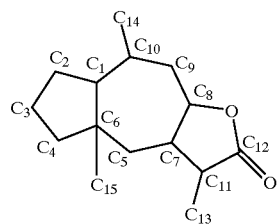

B

In formula B, $C_1$ is further bonded to hydrogen, hydroxy, short chain alkanoyloxy, or $C_2$ or $C_{10}$ via a double bond or an oxy linkage. $C_2$ is further bonded to at least one of the following substituents independently selected from the group consisting of hydrogen, hydroxy, oxo, short chain alkanoyloxy, and $C_1$ or $C_3$ via a double bond or an oxy linkage. $C_3$ is further bonded to at least one of the following substituents independently selected from the group consisting of hydrogen, oxo, and $C_2$ or $C_4$ via a double bond or an oxy linkage. $C_4$ is further bonded to at least one of the following substituents independently selected from the group consisting of hydrogen, hydroxy, short chain alkanoyloxy, and $C_3$ via an oxy linkage or a double bond. $C_6$ is further bonded to at least one of the following substituents independently selected from the group consisting of hydrogen, hydroxy, and short chain alkanoyloxy. $C_7$ is further bonded to hydrogen or $C_{11}$ via a double bond and $C_8$ is further bonded to hydrogen. $C_9$ is further bonded to at least one of the following substituents independently selected from the group consisting of hydrogen and $C_{10}$ via a double bond. $C_{10}$ is further bonded to hydrogen, hydroxy, short chain alkanoyloxy, $C_1$ or $C_{14}$ via an oxy linkage and $C_1$, $C_9$, or $C_{14}$ via a double bond. $C_{11}$ is further bonded to hydrogen, hydroxy, hydroxymethyl, or $C_7$ or $C_{13}$ via a double bond. $C_{13}$ is further bonded to at least one of the following substituents independently selected from the group consisting of hydrogen, an optionally substituted alkylamino salt, and $C_{11}$ via a double bond. $C_{14}$ is further bonded to at least one of the following substituents independently selected from the group consisting of hydrogen and $C_{10}$ via an oxy linkage or a double bond and $C_{15}$ is further bonded to three hydrogens.

The phosphosesquiterpene can be a phosphorylation product of the sesquiterpene lactone having formula C.

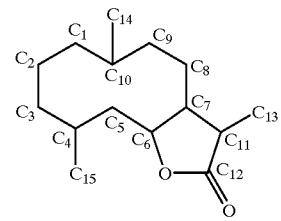

C

In formula C, $C_1$ is further bonded to at least one of the following substituents independently selected from the group consisting of hydrogen, hydroxy, oxo, short chain alkyl, short chain alkanoyloxy, $C_5$ via a single bond, $C_2$ via a double bond, and $C_{10}$ via an oxy linkage or a double bond. $C_2$ is further bonded to at least one of the following substituents independently selected from the group consisting of hydrogen, oxo, hydroxy, short chain alkanoyloxy, and $C_1$ or $C_3$ via a double bond. $C_3$ is further bonded to at least one of the following substituents independently selected from the group consisting of hydrogen, hydroxy, short chain alkaoyloxy, oxo, $C_4$ via an oxy linkage, and $C_2$ or $C_4$ via a double bond. $C_4$ is further bonded to hydrogen, short chain alkanoyloxy, hydroxy, or $C_3$, $C_5$, or $C_{15}$ via an oxy linkage or a double bond. $C_5$ is further bonded to at least one of the following substituents independently selected from the group consisting of hydrogen, hydroxy, short chain alkanoyloxy, $C_{10}$ or $C_1$ via a single bond, and $C_4$ via an oxy linkage or a double bond. $C_6$ is further bonded to hydrogen and $C_7$ is further bonded to hydrogen, or $C_8$ or $C_{11}$ via a double bond. $C_8$ is further bonded to at least one of the following substituents independently selected from the group consisting of hydrogen, hydroxy, short chain alkanoyloxy, and $C_7$ via a double bond. $C_9$ is further bonded to at least one of the following substituents independently selected from the group consisting of hydrogen, short chain alkanoyloxy, and $C_{10}$ via a double bond. $C_{10}$ is further bonded to at least one of the following substituents independently selected from the group consisting of hydrogen, $C_1$ or $C_{14}$ via an oxy linkage, $C_5$ via a single bond, and $C_1$ or $C_9$, $C_{14}$ via a double bond. $C_{11}$ is further bonded to hydrogen, hydroxy, hydroxymethyl, or $C_7$ or $C_{13}$ via a double bond. $C_{13}$ is further bonded to at least one of the following substituents independently selected from the group consisting of hydrogen, an optionally substituted alkylamino salt, and $C_{11}$ via a double bond. $C_{14}$ is further bonded to at least one of the following substituents independently selected from the group consisting of hydrogen and $C_{10}$ via an oxy linage or a double bond. $C_{15}$ is further bonded to at least one of the following substituents independently selected from the group consisting of hydrogen and $C_4$ via an oxy linkage or a double bond.

The phosphosesquiterpene can be a phosphorylation product of the sesquiterpene lactone having formula D.

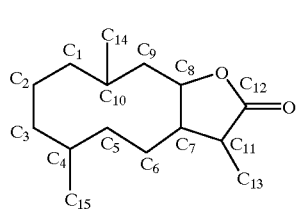

D

In formula D, $C_1$ is further bonded to at least one of the following substituents independently selected from the group consisting of hydrogen, hydroxyl, $C_{10}$ or $C_5$ via an oxy linkage, and $C_{10}$ or $C_2$ via a double bond. $C_2$ is further bonded to at least one of the following substituents independently selected from the group consisting of hydrogen, and $C_1$ via a double bond. $C_3$ is further bonded to at least one of the following substituents independently selected from the group consisting of hydrogen, hydroxy, short chain alkanoyloxy, and oxo. $C_4$ is further bonded to hydrogen, hydroxy, short chain alkanoyloxy, or $C_5$ or $C_{15}$ via an oxy linkage or a double bond. $C_5$ is further bonded to at least one of the following substituents independently selected from the group consisting of hydrogen, short chain alkanoic acid, $C_1$ or $C_4$ via an oxy linkage, $C_{10}$ via a single bond, and $C_4$ or $C_6$ via a double bond. $C_6$ is further bonded to at least one of the following substituents independently selected from the group consisting of hydrogen, hydroxy, short chain alkanoyloxy, and $C_5$ via a double bond. $C_7$ is further bonded to hydrogen, or $C_{11}$ via a double bond, $C_8$ is further bonded to hydrogen and $C_9$ is further bonded to two hydrogens. $C_{10}$ is further bonded to hydrogen, $C_5$ via a single bond, or $C_1$ or $C_{14}$ via an oxy linkage or a double bond. $C_{11}$ is further bonded to hydrogen, hydroxy, hydroxymethyl, or $C_7$ or $C_{13}$ via a double bond. $C_{13}$ is further bonded to at least one of the following substituents independently selected from the group consisting of hydrogen, an optioarally substituted alkylamino salt, and $C_{11}$ via a double bond. $C_{14}$ is further bonded to at least one of the following substituents independently selected from the group consisting of hydrogen and $C_{10}$ via an oxy linkage or a double bond. $C_{15}$ is further bonded to at least one of the following substituents independently selected from the group consisting of hydrogen and $C_4$ via an oxy linkage or a double bond.

The invention also features methods for inhibiting farnesyl-protein transferase. The method includes contacting a cell with an amount of a sesquiterpene lactone effective to inhibit farnesyl-protein transferase activity of the cell. The method can also include monitoring farnesyl-protein transferase activity. The sesquiterpene lactone can be selected from the group consisting of ambrosanolides, psilostachyanolides, cadinanolides, cremanolides, xanthanolides, guaianolides, germacranolides, elamanolides and eudesmanolides. A sesquiterpene lactone having the structure of formula A, B, C or D is particularly useful for inhibiting farnesyl-protein transferase activity.

In another aspect, the invention features a substantially pure preparation of a phosphosesquiterpene. The phosphosesquiterpene can have a skeletal structure of a compound selected from the group consisting of ambrosanolides, psilostachyanolides, cadinanolides, eremanolides, xanthanolides, guaianolides, germacranolides, elamanolides and eudesmanolides. The phosphosesquiterpene can include a gamma-lactone ring or a carboxylic acid substituent.

The phosphosesquiterpene can have formula E.

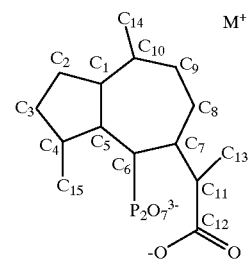

E $C_1$ of formula E is further bonded to hydrogen, hydroxy, short chain alkanoyloxy, or $C_2$ or $C_{10}$ via a double bond or an oxy linkage. $C_2$ is further bonded to at least one of the following substituents independently selected from the group consisting of hydrogen, hydroxy, oxo, short chain alkanoyloxy, and $C_1$ or $C_3$ via a double bond or an oxy linkage. $C_3$ is further bonded to at least one of the following substituents independently selected from the group consistig of hydrogen, oxo, and $C_2$ or $C_4$ via a doublebond or an oxy linkage. $C_4$ is further bonded to hydrogen, hydroxy, short chain alkanoyloxy, or $C_3$, $C_5$, or $C_{15}$ via an oxy llnkage or a double bond. $C_5$ is further bonded to hydrogen, hydroxy, short chain alkanoyloxy, or $C_4$ via an oxy linkage or a double bond. $C_6$ is further bonded to hydrogen and $C_6$ is further bonded to hydrogen or $C_{11}$ via a double bond. $C_8$ is further bonded to at least one of the following substituents independently selected from the group consisting of hydrogen, hydroxy, and short chain alkanoyloxy. $C_9$ is further bonded to at least one of the following substituents independently selected from the group consisting of hydrogen, and $C_{10}$ via a double bond. $C_{10}$ is further bonded to hydrogen, hydroxy, short chain alkanoyloxy, $C_1$ or $C_{14}$ via an oxy linkage, or $C_1$, $C_9$, or $C_{14}$ via a double bond. $C_{11}$ is further bonded to hydrogen, hydroxy, hydroxymethyl, or $C_7$ or $C_{13}$ via a double bond. $C_{13}$ is further bonded to at least one of the following substituents independently selected from the group consisting of hydrogen, an optionally substituted alkylamino salt, and $C_{11}$ via a double bond. $C_{14}$ is further bonded to at least one of the following substituents independently selected from the group consisting of hydrogen and $C_{10}$ via an oxy linkage or a double bond. $C_{15}$ is further bonded to at least one of the following substituents independently selected from the group consisting of hydrogen and $C_4$ via an oxy linkage or a double bond. $M^+$ is any combination of chemical entities which is able to neutralize any negative charges of the phosphosesquiterpene.

The phosphosesquiterpene can have formula F.

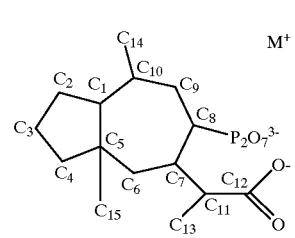

F

In formula F, $C_1$ is further bonded to hydrogen, hydroxy, short chain alkanoyloxy, or $C_2$ or $C_{10}$ via a double bond or an oxy linkage. $C_2$ is further bonded to at least one of the following substituents independently selected from the group consisting of hydrogen, hydroxy, oxo, short chain alkanoyloxy, and $C_1$ or $C_3$ via a double bond or an oxy linkage. $C_3$ is further bonded to at least one of the following substituents independently selected from the group consisting of hydrogen, oxo, and $C_2$ or $C_4$ via a double bond or an oxy linkage. $C_4$ is further bonded to at least one of the following substituents independently selected from the group consisting of hydrogen, hydroxy, short chain alInoyloxy, and $C_3$ via an oxy linkage or a double bond. $C_6$ is further bonded to at least one of the following substituents independently selected from the group consisting of hydrogen, hydroxy, and short chain alkanoyloxy. $C_7$ is further bonded to hydrogen or $C_{11}$ via a double bond and $C_8$ is further bonded to hydrogen. $C_9$ is further bonded to at least one of the following substituents independently selected from the group consisting of hydrogen and $C_{10}$ via a double bond. $C_{10}$ is further bonded to hydrogen, hydroxy, short chain alkanoyloxy, $C_1$ or $C_{14}$ via an oxy linkage and $C_1$, $C_9$, or $C_{14}$ via a double bond. $C_{11}$ is further bonded to hydrogen, hydroxy, hydroxymethyl, or $C_7$ or $C_{13}$ via a double bond. $C_{13}$ is further bonded to at least one of the following substituents independently selected from the group consisting of hydrogen, an optionally substituted alkylamino salt, and $C_{11}$ via a double bond. $C_{14}$ is further bonded to at least one of the following substituents independently selected from the group consisting of hydrogen and $C_{10}$ via an oxy linkage or a double bond. $C_{15}$ is further bonded to three hydrogens. $M^+$ is any combination of chemical entities which is able to neutralize any negative charges of the phosphosesquiterpene.

The phosphosesquiterpene can have formula G.

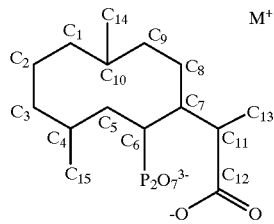

G

In formula G, $C_1$ is further bonded to at least one of the following substituents independently selected from the group consisting of hydrogen, hydroxy, oxo, short chain alkyl, short chain alkanoyloxy, $C_5$ via a single bond, $C_2$ via a double bond, and $C_{10}$ via an oxy linkage or a double bond. $C_2$ is further bonded to at least one of the following substituents independently selected from the group consisting of hydrogen, oxo, hydroxy, short chain alkanoyloxy, and $C_1$ or $C_3$ via a double bond. $C_3$ is further bonded to at least one of the following substituents independently selected from the group consisting of hydrogen, hydroxy, short chain alkanoyloxy, oxo, $C_4$ via an oxy luinage, and $C_2$ or $C_4$ via a double bond. $C_4$ is further bonded to hydrogen, short chain alkanoyloxy, hydroxy, or $C_3$, $C_5$, or $C_{15}$ via an oxy linkage or a double bond. $C_5$ is further bonded to at least one of the following substituents independently selected from the group consisting of hydrogen, hydroxy, short chain alkanoyloxy, $C_{10}$ or $C_1$ via a single bond, and $C_4$ via an oxy linkage or a double bond. $C_6$ is further bonded to hydrogen and $C_7$ is further bonded to hydrogen, or $C_8$ or $C_{11}$ via a double bond. $C_8$ is further bonded to at least one of the following substituents independently selected from the group consisting of hydrogen, hydroxy, short chain alkanoyloxy, and $C_7$ via a double bond. $C_9$ is further bonded to at least one of the following substituents independently selected from the group consisting of hydrogen, short chain alkanoyloxy, and $C_{10}$ via a double bond. $C_{10}$ is further bonded to at least one of the following substituents independently selected from the group consisting of hydrogen, $C_1$ or $C_{14}$ via an oxy linkage, $C_5$ via a single bond, and $C_1$ or $C_9$, $C_{14}$ via a double bond. $C_{11}$ is further bonded to hydrogen, hydroxy, hydroxymethyl, or $C_7$ or $C_{13}$ via a double bond. $C_{13}$ is further bonded to at least one of the following substituents independently selected from the group consisting of hydrogen, an optionally substituted alkylamino salt, and $C_{11}$ via a double bond. $C_{14}$ is further bonded to at least one of the following substituents independently selected from the group consisting of hydrogen and $C_{10}$ via an oxy linkage or a double bond. $C_{15}$ is further bonded to at least one of the following substituents independently selected from the group consisting of hydrogen and $C_4$ via an oxy linkage or a double bond. $M^+$ is any combination of chemical entities which is able to neutralize any negative charges of the phosphosesquiterpene.

The phosphosesquiterpene can have formula H.

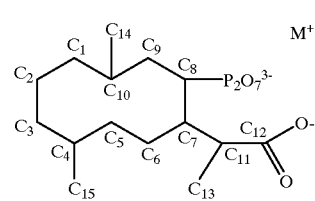

H

In formula H, $C_1$ is further bonded to at least one of the following substituents independently selected from the group consisting of hydrogen, hydroxyl, $C_{10}$ or $C_5$ via an oxy linkage, and $C_{10}$ or $C_2$ via a double bond. $C_2$ is further bonded to at least one of the following substituents independently selected from the group consisting of hydrogen, and $C_1$ via a double bond. $C_3$ is further bonded to at least one of the following substituents independently selected from the group consisting of hydrogen, hydroxy, short chain alkanoyloxy, and oxo. $C_4$ is further bonded to hydrogen, hydroxy, short chain alkanoyloxy, or $C_5$ or $C_{15}$ via an oxy linkage or a double bond. $C_5$ is ftrther bonded to at least one of the following substituents independently selected from the group consisting of hydrogen, short chain alkanoic acid, $C_1$ or $C_4$ via an oxy linkage, $C_{10}$ via a single bond, and $C_4$ or $C_6$ via a double bond. $C_6$ is further bonded to at least one of the following substitnents independently selected from the group consisting of hydrogen, hydroxy, short chain alkanoyloxy, and $C_5$ via a double bond. $C_7$ is further bonded to hydrogen, or $C_{11}$ via a double bond and $C_8$ is further bonded to hydrogen. $C_9$ is further bonded to two hydrogens and $C_{10}$ is further bonded to hydrogen, $C_5$ via a single bond, or $C_1$ or $C_{14}$ via an oxy linkage or a double bond. $C_{11}$ is further bonded to hydrogen, hydroxy, hydroxymethyl, or $C_7$ or $C_{13}$ via a double bond. $C_{13}$ is further bonded to at least one of the following substituents independently selected from the group consisting of hydrogen, an optionally substituted alkylamino salt, and $C_{11}$ via a double bond. $C_{14}$ is further bonded to at least one of the following substituents independently selected from the group consisting of hydrogen and $C_{10}$ via an oxy linkage or a double bond. $C_{15}$ is further bonded to at least one of the following substituents independently selected from the group consisting of hydrogen and $C_4$ via an oxy linkage or a double bond. $M^+$ is any combination of chemical entities which is able to neutralize any negative charges of the phosphosesquiterpene.

The invention also relates to a pharmaceutical composition in, unit dosage form that includes a phosphosesquiterpene. The composition is suitable for the treatment of a human cancer including breast, colon, rectal, stomach, pancreatic, lung, liver, ovarian, leukemia, lymphoma, pancreatic and esophageal cancer. The composition is particularly useful for the treatment of lung, liver, and ovarian cancer. The phosphosesquiterpene can be phosphorylated diinethylaminoarglabin or a pharmaceutically acceptable salt thereof, and can be lyophilized. The unit dosage of phosphorylated dimethylaminoarglabin or a pharmaceutically acceptable salt thereof can range from about 0.5 mg/kg to about 7 mg/kg, and is particularly useful from about 3.4 mg/kg to about 4.0 mg/kg.

The invention also features an article of manufacture including packaging material and a pharmaceutical agent contained within the packaging material. The packaging material includes a label that indicates that the pharmaceutical agent can be used for suppressing tumor growth in a human. The pharmaceutical agent includes a phosphosesquiterpene. Phosphorylated dimethylaminoarglabin or a pharmaceutically acceptable salt thereof are particularly useful phosphosesquiterpenes.

As used herein, phosphate or phospho group refers to pyrophosphate or orthophosphate. A phosphorylation product refers to a product obtained from a phosphorylation reaction performed on a sesquiterpene lactone. "Skeletal structure" refers to the carbon framework of a compound. For example, the 15-carbon frameworks found in formulas A-H are skeletal structures. As used herein, two carbon atoms linked to each other via an oxy linkage means that an oxirane or epoxide structure is formed. The term "short chain alkyl" includes methyl, ethyl, propyl, isopropyl, n-butyl, isobutyl, sec-butyl, and tert-butyl substituents. "Short chain alkanoyloxy" includes acetoxy, propioinyloxy, n-butyryloxy, iso-butyryloxy, sec-butyryloxy, and tert-butyryloxy substituents. "Short chain alkanoic acid" includes formic acid, acetic acid, propionic acid, n-butyric, iso-butyric, sec-butyric, and tert-butyric acid substituents. "Optionally substituted alkylamino salts" include N,N-di (short chain alkyl)amino hydrogen chloride salts.

"$M^+$" refers to any chemical entity or combination of chemical entities that is able to neutralize any negative charges that are present in the phosphosesquiterpenes of the invention. These negative charges typically arise from dissociation of acidic hydrogens from heteroatoms present on the compounds, for example, the oxygen atoms of carboxylic or phosphate substituents. It is recognized that these acidic hydrogens may be fully ionized, partially ionized, or un-ionzied under different conditions. Thus $M^+$ can be any combination of hydrogen, or any alkali metal cation, preferably sodium or potassium. The chemical entities represent by $M^+$ may also have the ability to neutralize multiple negative charges in the phosphosesquiterpenes of the invention.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWING

FIG. 1 is a table that describes the putative site of attachment of a pyrophosphate group in the featured phosphosesquiterpenes.

FIG. 2 illustrates the putative site of sesquiterpene lactone phosphorylation.

FIG. 4 is a chromatogram that depicts the absence of the farnesylcysteine derivative after incubation with dirnethylaminoargiabin hydrochloride.

FIG. 11 is a graph that depicts the amount of bioluminescence after incubation of cell lysates from Ras-transfected NIH3T3 cells with water (circles), dimethylaminoarglabin hydrochloride (squares) or mevalonolactone (triangles).

FIG. 12 is a graph that depicts the amount of bioluminescence after incubation of liver lysates with water (circles), dimethylaminoarilabin hydrochloride (squares) or mevalonolactone (triangles).

FIG. 13 is a graph that depicts the amount of bioluminescence after incubation of cell lysates from Ras-transfected NIH3T3 cells with water (circles), arglabin (squares) or dimethylaminoarglabin hydrochloride (triangles).

DETAILED DESCRIPTION

Figure 3:
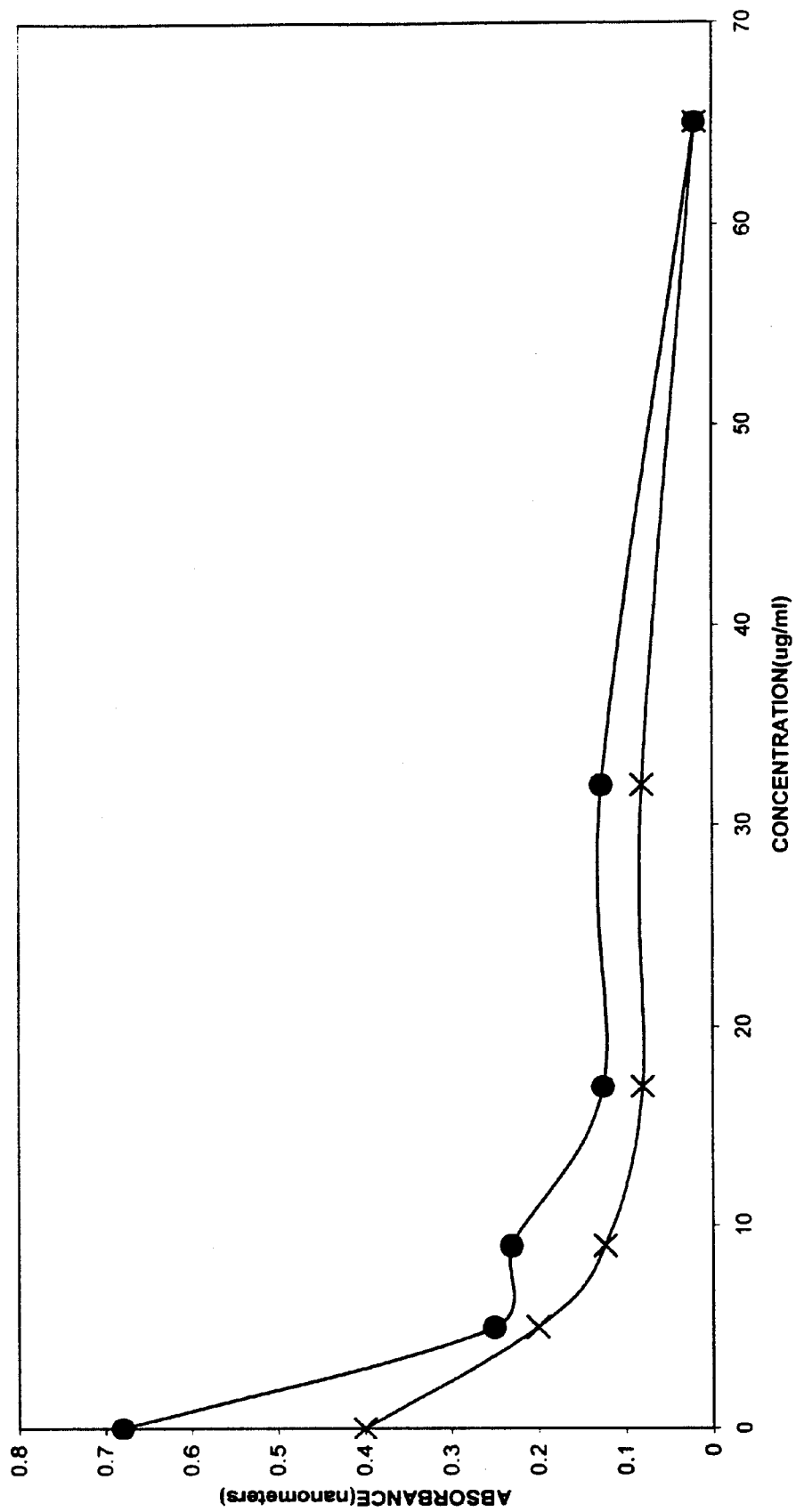
FIG. 3 is a graph that correlates β-galactoside activity (absorbance, nm) to drug concentration. Circles represent experiments in the absence of cloprostenol and X's represent experiments in the presence of cloprostenol.

General methods of extracting sesquiterpene lactones from plants and of preparing sesquiterpene lactones by chemical synthesis are described below. Sesquiterpene lactones are phosphorylated in vitro or in vivo to obtain phosphosesquiterpene compounds that inhibit farnesyl protein transferase.

Extraction of Sesquiterpene Lactones From Plants

At least nine classes of sesquiterpene lactones have been identified in plants. The simplest biosynthetic class includes the germacranolides. The more advanced biosynthetic classes, the elamanolides, eudesmanolides, guaianolides, cadinanolides, eremanolides, ambrosanolides, xanthanolides and the psilostachyanolides can be obtained by cyclization, rearrangements and oxidation of the germacranolides. Kelsey, R. G. and Shafzadeh, F., 1979, Phytochem., 18:1591–1611.

Sesquiterpene lactones can be isolated from a variety of plants, including plant species in the genuses Grosshimia, Chrysanthemum, Achillea, Schisostephium, Jurinea, Inula and Artemisia. For example, sesquiterpene lactones can be isolated from *A. glabella* Kar et. Kir, *A. arborescens, A. Adotzchiana, A. cana, A. tripartita, A. fragrans, A. absinthium, A. maritima* L., *A. Mexicana, A. pauciflora* Web, *A. douglasiana, A. ludoviciana, A. nova, A. herba alba, A. arbuscula* and *A. ashurbajevii*.

In general, sesquiterpene. lactones are isolated from the stems, leaves, flowers or flower buds of plants by solvent extraction and chromatography. Extractions are typically performed at room temperature using vanous solvents or solvent combinations, including chloroform, water, diethyl ether, benzene and ethanol. After removal of solvent, the remaining tar can be further extacted, for example, with an aqueous ethanol solution or can be separated into individual components by silica, alumina or Florisil® chromatography. Typical eluants include benzene, chloroform, hexane, acetone, methanol, ethyl acetate or combinations of these solvents. Purification of the sesquiterpene lactones can be assessed by routine measures, including, for example, thin-layer chromatography. Individual sesquiterpene lactones can be further purified or crystallized using standard chemical methods.

For example, arglabin can be extracted from *A. glabella* with an appropriate solvent such as chloroform and refmed from the solvent in the form of a tar. Arglabin can be precipitated from the tar with aqueous ethanol and purified using silica chromatography, as described below in Example 1.

The sesquiterpene lactone estafiatin can be extracted from *A. mexicana* with ethanol under reflux for about 8 hours. After concentration, the extact can be treated with an aqueous lead acetate solution at room temperature for about 2 hours. The extract can be filtered, diluted with water and extracted with chloroform. Solvent can be removed by evaporation and the remaining residue can be dissolved in benzene:hexane (1:1) or other suitable solvent and chromatographed on alumina Estafiatin can be eluted from the column with benzene:hexane. Romo, 3. et al., *Phytochemistry*, 1970, 9:1615–1621.

The sesquiterpene lactone grosshemin can be extracted from *Grosshimia macrocephala, Chartolepis intennedia* or *Centaure aruthenica* as described by Adekenov, S. M. et al., (1986), *Khimiko-Farmatsevticheskii Zhurnal.*, 20(8):938–942.

The sesquiterpene lactone inuchinenolide C can be extracted from the whole plant of *Inula britannica* Var. chinensis as described by Ito, K. and Iida, T., (1981), *Phytochemistry*, 20(2):271–274. Inuchinenolide C can also be etracted from the flowers and leaves of *Inula caspica* using standard extraction procedures.

Chemical Synthesis of Sesquiterpene Lactones and Detivatives

Sesquiterpene lactones can be chemically synthesized using methods described by Heathcock, C. H. et al., In *The Total Synthesis of Natural Products*, Apsimon, J. W., Ed. Wiley: New York, 1982, Vol. 5. In particular, sesquiterpene lactones of the guaianolide series can be synthesized by skeletal isomerization of mono-, bi- or tri-cyclic precursors, pentacondensation of cycloheptane derivatives or from functionalized cyclopentanes. Zhuzbaev, B. T. et al., (1995), *Russian Chem. Rev.*, 64(2):187–200. Grosshemin can also be chemically synthesized. See, for example, Rigby, J. H. and Senanayake, C., (1987), *J. Amer. Chem. Soc.*, 109(10):3147–3149.

In general, dimethylamino derivatives of the sesquiterpene lactones can be synthesized by dissolving the sesquiterpene lactone in ethanol or other suitable solvent and reacting with a dimethylamine solution. After amination is complete, the mixture can be heated and solvent can be removed by vacuum distillation. The dimethylamino derivatives can be purified by one or more chloroform extractions and silica chromatography. Pharmaceutically acceptable dimethylamino salts can be prepared, for example, by reacting an alcohol solution of the dimethylamino derivative with sodium chloride and concentrated sulfuinc acid. Solvent can be removed, by vacuum distillation, leaving a tar behind. Hydrochloride salts are precipitated from the tar by addition of ethylacetate.

Preparation of Phosphosesquiterpenes

The featured sesquiterpene lactones generally inhibit cell proliferation of transformed cell lines when added at low concentrations and also have chemotherapeutic properties when administered to humans. As discussed herein, the sesquiterpene lactones of the invention inhibit the farnesylation of Ras protein. It has been discovered that the sesquiterpene lactones are activated by phosphorylation and are most likely competitive inhibitors of FPP.

Phosphosesquiterpenes of the invention possess mono-, bi-, or tricyclic carbon skeletons, and can further include a gamma-lactone ring and/or at least one carboxylic acid substituent. The skeletal structure of a phosphosesquiterpene can be selected, for example, from the ambrosanolide, psilostachyanolide, cadinanolide, eremanolide, xanthanolide, guaianolide, germacranolide, elamanolide or eudesmanolide classes of sesquiterpene lactones. A putative site of attachment for a pyrophosphate group is at the carbon shown in FIG. 1. This carbon was the gamma carbon in the former lactone ring of the sesquiterpene lactone. The pyrophosphate group may alternatively or additionally be bonded to the skeleton at sites other than this carbon atom, such as any carbon capable of bearing a hydroxy, epoxy, akianoyloxy, or alkanoic acid substituent. As shown in FIG. 2, the lactone ring may be opened to form the corresponding carboxylic acid and diphosphate.

Substantially pure preparations of phosphosesquiterpenes can be obtained by chemical synthesis or enzymatically using purified kinases or cell lysates as enzyme sources. As used herein, "substantially pure preparation" refers to a phosphosesquiterpene that has been separated from components that naturally accompany it. Typically, the phosphosesquiterpene is substantially pure when it is at least 60%, by weight, free from naturally-occurring organic molecules or proteins with which it is naturally associated. Preferably, the preparation is at least 75%, more preferably at least 90%, and most preferably at least 99%, by weight phosphosesquiterpene. For example, a phosphosesquiterpene can be chemically synthesized by incubating a substantially pure sesquiterpene lactone with ATP in buffer at about 70° C. Alternatively, a substantially pure sesquiterpene lactone can be incubated with an appropriate kinase, ATP and buffer in vitro to obtain a phosphosesquiterpene. For example, a kinase that phosphorylates mevalonolactone would be particularly suitable fdr phosphorylating the featured sesquiterpene lactones.

A phosphosesquiterpene can also be obtained by culturing cells with a sesquiterpene lactone for a period of time sufficient for the sesquiterpene lactone to be taken-up and phosphorylated by the cells.

A substantially purified sesquiterpene lactone can also be incubated with a cellular lysate in the presence of ATP to obtain a phosphosesquiterpene. Lysates may be prepared from cultured cells or from isolated tissue such as liver. In general, cultured cells are prepared for lysis by washing in phosphatebuffered saline (PBS) prior to harvesting, then incubating with a lysis buffer in the cold and homogenizing, for example, by briefly sonicating. Tissue samples are minced and then homogenized in the presence of a lysis buffer. Lysis buffers can include non-ionic detergents such as Igepal CA-630 (Sigma), chelating agents such as EDTA and EGTA, or high or low salt concentrations. Proteolytic activity within a lysate can be minimized by including various protease inhibitors. A typical lysis buffer can include, for example, 20 mM Tris buffer, pH 7.4, 1 mM $MgCl_2$ and 1 mM EGTA. After lysis, the lysate is centrifuged in the cold, i.e. 4° C., at 10,000–12,000×g for 2–5 minutes. The supernatant is removed and used for phosphorylating the sesquiterpene lactone. The lysate can be incubated with a sesquiterpene lactone and ATP to obtain phosphorylated sesquiterpene.

For example, 200 $\mu$M of sesquiterpene lactone and 200 $\mu$M ATP can be incubated with a lysate at 37° C. for 40 minutes to obtain a phosphosesquiterpene. Phosphorylated sesquiterpenes can be isolated from the lysate by ultra filtration, for example, by centrifugation through ultrafree-20 (Millipore) at 2,500×g for 30 minutes. The filtrate can be lyophilized and dissolved in a small volume of water. Phosphorylated products obtained in this manner prevent farnesylation of Ras proteins.

Methods of Monitoring Farnesylation of Ras Protein

The farnesylation of Ras proteins can be monitored by incubating recombinant Ras protein, a cellular lysate containing a phosphosesquiterpene, and labeled-FPP with appropriate buffer. Reactions are ternated after a sufficient period of incubation to allow transfer of the farnesyl moiety to Ras protan The relative amount of farnesylated Ras protein can be estimated, for example, by electrophoresis through SDS-PAGE and transfer to nitrocellulose, followed by autoradiography.

Alternatively, the farnesyl transferase activity of bovine or human FPT can be assayed in the presence of a phosphosesquiterpene. Partially purified bovine or human FPT can be prepared as described by Schaber et al., (1990), *J. Biol. Chem.*, 265:14701–14704, and Omer et al., (1992), *Biochemistry*, 32:5167–5176, respectively. Bovine FPT can be assayed in a reaction containing a phosphosesquiterpene test compound, 100 mM HEPES buffer, pH 7.4, 5 mM $MgCl_2$, 5 mM dithiothreitol (DTT), 100 mM [$^3$H]-FPP, Ras peptides and 10 $\mu$g/mg bovine FPT. The reactions are incubated at 31° C. for 60 minutes and terminated by addition of 1 ml of 1.0 M HCl in ethanol. Precipitates can be collected onto filter-mats using a cell harvester, washed with 100% ethanol, dried and counted in a β-counter. Human FPT can be assayed in a similar manner with the exception that 0.1% (w/v) polyethylene glycol 20,000 and 10 $\mu$M $ZnCl_2$ are added to the reaction mixture. Human FPT reactions can be stopped with 0.1 ml of 30% trichloroacetic acid in ethanol. Percentage inhibition is measured, by the amount of incorporation of radioactivity in the presence of a test compound when compared to the amount of incorporation in the absence of a test compound.

Pharmaceutical Compositions

The phosphosesquiterpenes of the invention can be formulated into pharmaceutical compositions by admixture with pharmaceutically acceptable non-toxic excipients or carriers. By "pharmaceutically acceptable carrier", it is meant that the carrier, diluent or excipient is compatible with the other ingredients of the formulation and not deleterious to the recipient thereof. Such compounds and compositions can be prepared for parenteral administration, particularly in the form of liquid solutions or suspensions in aqueous physiological buffer solutions; for oral administration, particularly in the form of tablets or capsules; or for intranasal adrinsbaton, particularly in the form of powders, nasal drops, or aerosols. Compositions for other routes of administration can be prepared as desired using standard methods.

A compound of the invention can be conveniently administered in unit dosage form, and can be prepared by any of the methods well known in the pharmaceutical art, for example, as described in *Remingon's Pharmaceutical Sciences* (Mack Pub. Co., Easton, Pa., 1980). As used herein, "unit dosage form" refers to physically discrete units suitable as unitary dosages for human subjects and other mammals, each unit containing a predetermined quantity of active material calculated to produce the desired therapeutic effect, in association with the pharmaceutically acceptable carrier. Formulations for parenteral adminision can contain as common excipients sterile water or saline, polyalkylene glycols such as polyethylene glycol, oils of vegetable origin, hydrogenated naphthalenes, and the like. In particular, biocompatible, biodegradable lactide polymer, lactide/glycolide copolymer, or polyoxethylene-polyoxypropylene copolymers are examples of excipients for controlling the release of a compound of the invention in vivo. Other suitable parenteral delivery systems include ethylene-vinyl acetate copolymer particles, osmotic pumps, implantable infusion systems, and liposomes. Formulations for inhalation administration can contain excipients such as lactose, if desired. Inhalation formulations can be aqueous solutions containing, for example, polyoxyetdylene-9-lauryl ether, glycocholate and deoxycholate, or they can be oily solutions for administration in the form of nasal drops. If desired, the compounds can be formulated as a gel to be applied intranasaly. Formulations for parenteral administration can also include glycocholate for buccal admirtstrfon.

The phosphosesquiterpenes can be administered to human patients in a daily amount from about 7 mg to about 700 mg (about 0.1 mg/kg to about 10 mg/kg), preferably from about 70 mg to about 490 mg (about 1 mg/kg to about 7 mg/kg), more preferably from about 140 mg to about 350 mg (about 2 mg/kg to about 5 mg/kg). In particular, phosphodimethylaminoarglabin or a pharmaceutically acceptable salt thereof can be administered to human patients in adaily amount from about 40 mg to about 480 mg (about 0.5 mg/kg to about 7 mg/kg), preferably from about 175 mg to about 315 mg (about 2.5 mg/kg to about 4.5 mg/kg), more preferably from about 240 mg to about 280 mg (about 3.4 mg/g to about 4 mg/kg). Similar dosages can be applied to non-human mammalian patients as required. In extreme conditions, up to about 20 mg/kg of a phosphorylated sesquiterpene may be administered. Once administered, these compounds act as antitumor agents and may inhibit the growth of tumors or may cause tumors to regress. The optimal concentration of the phophorylated sesquiterpene compound in a pharmaceutically acceptable composition can vary, depending on a number of factors, including the preferred dosage of the compound to be administered, the chemical characteristics of the compounds employed, the formulation of the compound excipients and the route of administration. The optimal dosage of a pharmaceutical composition to be administered can also depend on such variables as the type and extent of cancer metastases, the overall health status of the particular patient and the relative biological efficacy of the compound selected. These compositions can be used for the treatment of cancer, especially lung, liver and ovarian cancer, although other cancers such as breast, rectal, colon, stomach, pancreatic or esophageal cancer are also beneficially treated with the compositions. In addition, hematopoietic cancers such as leukemias and lymphomas may also be beneficially treated.

In an alternative embodiment, a pharmaceutical composition containing from about 7 mg to about 700 mg (about 0.1 mg/kg to about 10 mg/kg), preferably from about 70 mg to about 490 mg (about 1 mg/kg to about 7 mg/kg), more preferably from about 140 mg to about 350 mg (about 2 mg/kg to about 5 mg/kg) of a phosphosesquiterpene is provided in unit dosage form. The dose may be divided into 2–4 daily doses. In extreme conditions, up to about 20 mkg may be administered. In particular, a pharmaceutical composition containing from about 40 mg to about 480 mg (about 0.5 mg/kg to about 7 mg/kg), preferably from about 175 mg to about 315 mg (about 2.5 mg/kg to about 4.5 mg/kg), more preferably from about 240 to about 280 mg (about 3.4 mg/kg to about 4 mg/kg) of phosphorylated dimethylaminoarglabin or a pharmaceutically acceptable salt is provided in unit dosage form Lyophilized phosphorylated dimethylaminoarglabin and pharmaceutically acceptable salts thereof are particularly useful as pharmaceutical compositions.

The invention will be further described in the following examples, which do not limit the scope of the invention described in the claims.

EXAMPLES

Example 1
Extraction of Arglabin From *Artemisia glabella*

An extraction device consisting of a counter-flow continuous extractor, loading device and three vessels isolated from the exterior environment was used for the extractions. The solvent vessel had a filter, distillator with an evaporator and condenser, and a buffer capacity. The drying agent vessel consisted of a dryer, cyclone, cooler, ventilator and heater. The cooling water vessel included a saltpan with ventilation. The extraction device also had a deodorizer with ventilator, a waste tank and an extract collector.

Approximately 7.7 kg of dry material from *Artemisia glabella* Kar. et Kir. was placed in the extraction device and continuously mixed with solvent as the material was moved through the extractor column. The solvent moved in a direction opposite that of the dry plant material and gradually became saturated with extracted substances. As the saturated solvent was discharged, it was first filtered to remove plant material particles, then evaporated. The filtered plant particles were recirculated through the extractor for re-extraction. Vapors from the evaporation were sent to the condenser. From the condenser, pure solvent was recovered and recirculated to the extraction device. Condensation surfaces in the condenser were cooled with water pumped from the salt pan where the water was previously cooled with exterior air blown in the ventilator. Due to airvaporized cooling in the salt pan, the water may be cooled to temperatures considerably lower than the ambient temperature.

The extracted substances refined from the solvent were in the form of a tar. During this process, approximately 7% of the plant material (539 grams) was recovered.

The tar was further refined by addition of two volumes (approximately 1.08 L) of 60° C. ethanol with continuous stirring to dissolve the tar. Distilled water, heated to approximately 70° C., was added in a ratio of about 2:1 alcohol to water. The tar-alcohol-water solution was thoroughly stirred for 30 minutes, then left at room temperature for approximately 24 hours or until a precipitate was formed. The water alcohol solution was filtered through a ceramic filter under vacuum. The procedure was repeated with any precipitate remaining after filtration.

The filtrate was rotary evaporated and the alcohol was vacuum distilled in the form of an azeotropic mixture with water containing 68–70% alcohol. After distillation of the alcohol, the water solution yielded approximately 286 grams of refined tar.

The refined tar was separated into individual components over a KCK silicagel column, with pressure, using benzene as the eluant. Benzene fractions were collected and analyzed for aiglabin using thin-layer chromatography (TLC) (Silufol, benzene-ethanol, 9:1). Arglabin-containing fractions were distilled to remove benzene. Arglabin at this stage had a yellow color. Approximately 33 g of arglabin was produced, with a yield of about 11.7% from refined tar.

Arglabin was recrystallized by dissolving in hexane in a 1:10 ratio of product to hexane (w/v) and heating. After arglabin was in solution, the product was vacuum filtered. Crystals of arglabin were isolated from the filtrate at room temperature. Approximately 21 g of arglabin was recovered from this step. Arglabin has a structure of 1(R), 10(S)-epoxy-5(S), 6(S), 7(S)-guaia-3(4), 11(13)-diene-6,12-olide. The stereochemistry of arglabin was determined through x-ray analysis.

The NMR spectrum of arglabin was recorded on a Vanran HA-100D apparatus in $CDCl_3$. Chemical shifts are given in δ-scale from signal TMS accepted for 0. There are two three-proton singlets at 1.34 (methyl at epoxide) and at 1.94 ppm (methyl at double bond). A single-proton doublet was registered at 2.95 ppm with J=10 Hz (proton at C). A single-proton triplet was detected with the center at 3.97 ppm with J=10 Hz (lactone proton). Two single-proton doublets were obtained at 5.42 ppm with J=3 Hz and 6.1 ppm with J=3 Hz (exomethylene at lactone cycle) and a single-proton signal at 5.56 (vinyl proton). The structure of arglabin (FIG. 1) was confirmed on the basis of the NMR spectrum of the isolated compound and that of related sesquiterpene lactones arborescien and ludartine.

Summary of arglabin characteristics: Colorless, Melting Point of approximately 100–102° C. (hexane); $[\alpha]^{20}_D$+45.6° (c 0.3, $CHCl_3$); IR bands (KBr) 1760, 1660, 1150, 1125 $cm^{-1}$; $^1$H-NMR (400 MHz, $CDCl_3$) δ 1.34 (3H, s, H-14), 1.94 (3H, s, H-15), 2.95 (1H, d, J 10 Hz, H-5), 3.97 (1H, t, J 10 Hz, H-6), 5.56 (1H, br s, H-3), 5.42 (1H, d, J3 Hz, H-13a), 6.10 (1H, d, J 3 Hz, H-13b).

Example 2
Synthesis of Dimethylaminoarglabin Hydrochloride

Approximately 21 g of arglabin was mixed with 0.21 L of alcohol and heated to 40° C. until arglabin was fully dissolved. After filtering, a 33% solution of dimethylamine (0.023 L) was added dropwise with stirring. The mixture was left for 24 hours at room temperature. The reaction was monitored with TLC on Silufol plates. After the amination reaction was complete, the mixture was heated to 52° C. and the alcohol was vacuum distilled. Approximately 0.63 L of chloroform was added to the remaining solvent and stirred for 30 minutes. The mixture was poured into a separatory funnel where the chloroform found in the lower part of the funnel was collected. The chloroform extraction was repeated two additional times with the aqueous layer. Magnesium sulfate was used to dry the collected chloroform. The chloroform-magnesium sulfate mixture was stirred for 30 minutes, then vacuum filtered to remove the chloroform. Approximately 22 g of dimethylaminoarglabin was produced.

Dimethylaminoarglabin was purified by first dissolving in 5 volumes (w/v) of chloroform then mixing with about 3 volumes (w/w) of KCK silica gel. After evaporation of the solvent, the dry material was chromatographically separated on a KCK silica gel column made with a 1:22 ratio of adduct to sorbent The column was eluted by a mixture of petroleum ether and diethyl ether (1:1, 1:2). Fractions of approximately 14–17 mls were collected and monitored with TLC. Dimethylaminoarglabin was recrystallized from the fraction with chloroform and ether (1:1).

Summary of dimethylaminoarglabin characteristics: melting point 94.5–95.5° C., $[\alpha]^{21}_D$+47° (c 1.7, $CHCl_3$); elemental analysis 70.41% C, 8.7% H. 4.82% N ($C_{12}H_{25}O_3N$); IR (≧CHCl max) 3050–3000 (shoulder), 2940, 2860, 2835, 2780, 2410, 1770 (carbonyl lactone), 1650 (double bond), 1550–1530 (broad band), 1470, 1450, 1385, 1335, 1180, 1150, 1140, 1125 $cm^{-1}$ (epoxy group); MS (m/z, intensity in %) M+ HCl 291 (5.07, HCl), 247 (0.5), 188 (1,2), 115 (2,19), 105 (1,6), 97 (3,2), 77 (3,5), 70 (6,2), 67 (2,9), 58 (100); NMR (200 MHz, $CDCl_3$, δ scale; multiplet, P.P.M. KCCB) 1.90 (3H), 2.27 (6H), 4.00 (1H,)=9.5), broadened singlet 5.53 (1H), d.m. 2.66 (2H, J4=J2=5.5).

Dimethylaminoarglabin hydrochloride was produced by dissolving dimethylaminoarglabin with 0.22 L of alcohol and heating to 40° C. After vacuum filtration, hydrogen chloride gas was produced by addition of 0.2 kg of sodium chloride and drops of concentrated suililric acid. The reaction was monitored by TLC. When the reaction was complete, the mixture was heated to 52° C. and the ethanol was vacuum distilled. Approximately 0.9 L of ethylacetate was added to the remaining tar with intensive stiring. The resulting precipitate yielded approximately 21 g of dimethylaminoarglabin hydrochloride.

Approximately 0.1 L of chloroform was added to dissolve dimethylaminoarglabin hydrochloride, then distilled to remove the chloroform. The remaining tar was mixed with 0.83 L of ethylacetate with intensive stirring. The mixture was cooled to insure complete precipitation of the product.

The resulting precipitate was vacuum filtered to remove all solvent. The end product was vacuum dried over potassium perchlorate and dissolved with apyretic distilled water at a ratio of 2 grams of dry material to 100 ml of water. Yield of dimethylaminoarglabin hydrochloride was approximately 20 grams (95% of the estimated amount on this stage).

Summary of dimethylaminoarglabin hydrochloride characteristics: melting point 203–204° C. (ethanol-ether); $[\alpha]^{21}_D$+61.53° (c 0.52, $CHCl_3$); IR 33050–3000 (broad band), 2980, 2970 (intensive broad band, N-H); 2890, 2970, 2360–2300 (broad band), 1775 (carbonyl of lactone), 1650 (weak band), 1480, 1450, 1385, 1345, 1185, 1140–1120, 1100, 1065, 1040, 1010 $cm^{-1}$; MS (m/z, intensity in %) 291 (3.01, M+ HCl), 115 (2.19), 105 (1.5), 97 (3.2), 91 (4.0), 77 (3.5), 70 (16.2), 67 (2.9), 58 (100); NMR (200 MHz, $CDCl_3$, δ-scale, multiplet, p.p.m. KCCB) c. 1.30 (3H), c. 1.87 (3H), c. 2.87 (6H), d.m. 4.17 (1H, J1=J2=10 Hz), broadened singlet 5.55 (1H).

The water solution of diinethylaminoarglabin hydrochloride was filtered through a cotton-gauze plug or 8 layers of gauze, and a sterile Millipore filter to a sterile glass jar. The solution was vacuum pumped out of the jar into a measuring buret and aliquoted into 2 ml vials or ampules. The filled vials or ampules were maintained at −40° C. on sterile shelves for 24 hours prior to drying in a KC-30 lyophilizer or a LS-45 lyophilizer. After this tempering period, the drying process was started. The temperature was maintained at −40° C. for 2 hours, then was gradually increased to approximately 50° C. (plus or minus about 5° C.). The transition to approximately 50° C. occurred over about 12–13 hours of drying. The final temperature did not exceed +60° C. The total duration of drying time was 24 hours. After this, the vials with dry compound were immediately covered with caps and rolled. Ampules were soldered. Each vial or ampule contained about 0.04 g of the preparation.

Vials or ampules that were not sterile filtered were sterilized by autoclaving for 20 minutes at 120° C., with pressure of 1.2 Atm.

Alternatively, the prepared dimethylaminoarglabin hydrochloride water solution was filtered through a cotton-gauze plug or 8 layers of gauze. Approximately 200 ml of the solution were poured into 500 ml bottles, covered with cotton-gauze plugs and wrapped with oil-paper. The filled bottles were steried by autoclaving for 30 minutes at 120° C. with 1.2 Atm of pressure. The sterile solution was cooled to room temperature. Using sterile technique, 2 ml of the solution was poured into sterile 10 ml vials. The vials were then lyophilized as described above. After lyophilization each vial contained about 0.04 g of the compound.

Yield of the compound was 17 g, equaling 88.2% for this stage and 0.22% overall of dry natural material. The lyophilized material had a white-straw color and a bitter taste. Authenticity of the preparation was verified by determining its melting point and recording IR-, mass-, and NMR-spectra. The quality of the preparation was controlled by diluting 1 mg of the preparation with 0.2 ml of water. Addition of one drop of a saturated vanillin solution in concentrated sulfuric acid turned the mixture a violet color, indicating the presence of terpenes. Lyophilized material may be stored for three years.

Example 3
In-vitro Activity of Sesquiterpene Lactones

Various transformed cell lines were incubated with varying concentrations of sesquiterpene lactone compounds to determine their effects on viability and proliferation. In general, low concentrations of the sesquiterpene lactones stopped cell division, while higher concentrations led to increased levels of cell mortality.

Mouse mastocytoma (P-815), myeloma (Z-P3x63Ag8.653), human erthyroleukernia (K-562), NIH3T3, Ras-transfected NIH3T3 and Cos-7 cell lines were used. Cells were cultured in either DMEM medium or in RPMI-1640 medium supplemented with 10% fetal calf serum at 37° C. under 5% $CO_2$.

Viability of the cell lines was determined by tan blue exclusion. The proliferation of the transformed cells was assessed by incubating $^3$H-labeled thymidine in the media for 18 hours. At the end of the specified time period, the proliferation was measured by counting the amount of $^3$H-thymidine incorporated. Thymidine incorporation provides a quantitative measure of the rate of DNA synthesis, which is typically directly proportional to the rate of cell division. Altenatively, proliferation of the cell lines were assessed by the MIT assay, as described by Mosmann, T., *J. Immunol. Methods*, 65(1–2):55–63, 1983. In this assay, MTT ((3-(4,5-dimethylthiazol-2-yl)-2,5-diphenyl tetrazlium bromide) in phosphate-buffered saline (PBS) was added to cells in growth medium. After incubation at 37° C., MTT is cleaved in the mitochondria of metabolically active cells to the colored formazan product. Optical density of the formazan product was measured at a reference wavelength of 630 mn and a test wavelength of 570 nm after solubilization by 0.1 ml of 0.04 N HCl in isopropanol. The amount of formazan product is directly proportional to cell number.

Dimethylaminoarglabin hydrochloride produced a two fold reduction in viability of X.653 and K-562 cells at 6 μg/ml and 12 μg/ml, respectively. Approximately 75% of K-562 and X-653 cells were killed at a concentration of 12 μg/ml, and the same proportions of P-815 cells were killed at a concentration of about 25 μg/ml. Higher concentrations of dimethylaminoarglabin further reduced the viability of these transformed cells. Proliferation of X-653 and P-815 cells was effectively blocked at concentrations of 6 μg/ml and 12 μg/ml of dimethylaminoarglabin hydrochloride, respectively.

A dimethylaminoarglabin hydrochloride concentration of 1.5 μg/ml reduced NIH3T3 viable cell number by approximately 50% after a 24 hour incubation. At 4 μg/ml, all of the NIH3T3 cells were dead. Proliferation of NIH3T3 cells was arrested after a 24 hour incubation with dimethylaminoarglabin hydrochloride at a concentration of 4 μg/ml. After a 96-hour incubation with dimethylaminoarglabin hydrochloride, it was found that the growth rate of NIH3T3 cells decreased with increasing concentrations. At a dimethylaminoarglabin hydrochloride concentration of 0.5 μg/ml, the NIH3T3 cells were still growing, whereas growth was minimal at 4 μg/ml.

Cos-7 cells were less sensitive to dimethylaminoargli hydrochloride. It was found that Cos-7 cells were viable after a 24 hour incubation with 16 μg/ml of dimethylaminoarglabin hydrochloride. Cos-7 cells lost their ability to proliferate after a 96 hour incubation with 4 μg/ml dimethylaminoarglabin hydrochloride.

Higher concentrations of dimethylaminoarglabin hydrochloride were needed to inhibit the proliferation of Ras-transfected NIH3T3 cells. A sharp decrease in proliferation was observed between 6–12 μg/ml after a 24 hour incubation. Cells lost viability at concentrations greater than 24 μg/ml.

Inuchinenolide C dimethylamino hydrochloride (F.W. 447.5), grosshemin dimethylamino hydrochloride (F.W. 343.5) and grosshemin acetate dimethylamino hydrochloride (F.W. 385.5) were also tested for ability to prevent the growth of Ras-transfected NIH3T3 cells. Approximately 2.5 μg/ml of inuchinenolide C dimethylamino hydrochloride stopped the growth of Ras-transfected NIH3T3 cells after a 24 hour incubation. A concentration of 5 μg/ml and 10 μg/ml of grosshemin dimethylamino hydrochloride and grosshemin acetate dimethylamino hydrochloride, respectively, was necessary to stop the proliferation of Ras-transfeted NIH3T3 cells.

The proliferation of Ras-transfected NIH3T3 cells incubated with 5–10 μg/ml of inuchinenolide C dimethylamino hydrochloride, grosshemin dimethylamino hydrochloride or grosshemin acetate dimethylamino hydrochloride was inhibited within 72 hours, but all cells were alive. Similar results were observed when arglabin and dimethylaminoarglabin hydrochloride were used.

Example 4
Receptor Selection and Amplification Assay

In this assay, NIH3T3 cells coexpressing v-ras and β-galactosidase were used. v-ras is a form of a ras gene carried by a murine sarcoma virus. The transfected cells were obtained from Oncogene Research Products (catalog #RAK113). Inhibition of Ras decreased the basal proliferation response of the cells that was linked to β-galactosidase activity. Ligand-induced effects on proliferation were measured by determining the amount of β-galactosidase activity. The agonist cloprostenol was used to induce a response from the endogenous prostanoid FP receptor as a control for the maximal response of the cells.

NIH3T3 cells transiently transfected with v-ras were resuspended in DMEM medium. Approximately 50 μl of the cell suspension were added to each well of a 96-well plate to which 1 μm cloprostenol and various concentrations of dimethylaminoarglabin hydrochloride had already been added to each well. The final volume in each well was 100 μl. Control cells were cultured with the same concentration of dimethylaminoarglabin hydrochloride, but in the absence of cloprostenol. The plates were incubated for 4 to 5 days in a humidified 5% $CO_2$ incubator at 37° C. After the incubation period, the medium was removed from each well and 100 μl of o-nitrophenyl-β-D-galactopyranoside (ONPG), the chromogenic β-galactoside substrate, were added to each well and the wells incubated at 30° C. in a humidified chamber to allow color development. Absorbance was measured at 405 nm using a multiscan plate reader (Labsystem).

The results from this experiment are swnmarize in FIG. 3. Circles represent experiments in the absence of cloprostenol and X's represent experiments in the presence of cloprostenol. After receptor stimulation by cloprostenol, β-galactosidase activity was decreased two-fold and four-fold with 4 μg/ml and 8 μg/ml of dimethylaminoarglabin hydrochloride, respectively. Without receptor stimulation, a four-fold decrease in β-galactosidase activity was observed with 4 μg/ml of dimethylaminoarglabin hydrochloride. The similar results observed with and without cloprostenol indicate that dimethylaminoarglabin hydrochloride disrupted the function of Ras and was potent enough to overcome the maximal proliferation response of the cells stimulated with cloprostenol.

Example 5
Inhibition of Protein Prenylation

Mouse mycloma Pai cells (ATCC accession number CRL-1580) were cultured in the presence of 60 μM dimethylaminoarglabin hydrochloride. The cells were collected by centrflgation at 600×g for 10 minutes and then washed twice in PBS. Control cells were grown in the absence of drug. The cells were solubilized in lysis buffer (50 mM Tris, pH 7.4, 25 mM EDTA, 0.05% Tween, 0.01 M NaCl) for 30 minutes on ice. Lysates were made by homogenization for 5 minutes at 4° C. and precipitated by centrifugation at 12,000×g for 10 minutes. The supernatant was collected. Proteins were precipitated with trichloroacetic acid and then successively washed with ethanol and ethyl ether. A selective naphthol cleavage of the bond between isoprenoides and proteins was performed as described by Epstein, W. W et al., (1991) Proc. Natl. Acad. Sci. USA 88:9668–9670. In general, 5 mg of a potassium naphthoxide and naphthol 4:1 mixture were added to approximately 10 mg of precipitated protein. After addition of 50 μl of dimethylformamide, the tubes were gassed with argon, capped and heated to 100° C. for eight to 15 hours. Reaction products were extracted with hexane and analyzed by HPLC (Waters System) using a 0.4×15 cm reverse-phase Nova-Pac $C_{18}$ column. The column was eluted with 20% water in acetonitrile at a flow of 1.0 ml/minute. Napthol cleavage products were detected at 360 nm (FIG. 4) with a full-scale deflection of 0.01 A unit In the control (FIG. 4A), the farnesylcysteine derivative eluted at 4.5 minutes and the geranylgeranylcysteine derivative at 6 minutes. The molar ratio of geranylgeranyl to farnesylcysteine was 6.

The influence of dimethylaminoarglabin hydrochloride on cellular prenylation is shown in FIG. 4B. Using 60 μM of dimethyiaminoarglabin hydrochloride, the peak corresponding to the farnesylcysteine derivative does not appear on the chromatogram, while the geranylgeranyl peak appeared as in the control. This indicates that dimethyl-aminoarglabin hydrochloride can prevent farnesylation of proteins without significant effects on geranylgeranylation.

Example 6
Inhibition of Farnesylation of Ras Protein

Cell lysates from Ras-transfected NIH3T3 cells were prepared and used to monitor the incorporation of a labeled farnesyl moiety onto Ras proteins.

Ras-transfected NIH3T3 cells in DMEM medium were incubated alone or with 5 μg/ml, 10 μg/ml or 15 μg/ml of dimethylaminoarglabin hydrochloride for 12 hours at 37° C. Control cells were grown in the absence of drug. After removal of the medium, cells were washed twice with 4° C. PBS, incubated in lysis buffer consisting of 20 mM Tris buffer, pH 7.4, 1 mM $MgCl_2$ and 1 mM EGTA, and briefly sonicated. The lysates were centrifuged at 10,000×g for 5 minutes. Protein concentrations were determined by the BCA protein assay kit (Sigma). The supernatant (S10) was used for all experiments.

A reaction containing 20 mM Tris-Cl, pH 7.5, 10 mM MgCl2, 1 mM dithiothreitol, 2 mg/ml S10 and 4 μg of recombinant human H-Ras protein was mixed and initiated by addition of 10 μM (2 μCi) $^3$H-farnesylpyrophosphate (22.5 Ci/mmol). After incubation for 40 minutes at 37° C. to allow transfer of the farnesyl moiety to Ras protein, the reaction was terminated by addition of 25 μl of 2×SDS/PAGE sample buffer (125 mM Tris-HCl, pH 6,8, 10% glycerol, 5% 2-mercaptoethanol. 0.02% bromophenol blue and 6% urea). Samples were boiled, electrophoresed through 12% SDS-PAGE and transferred to nitrocellulose by electroblotting, followed by autoradiography.

Figure 5:
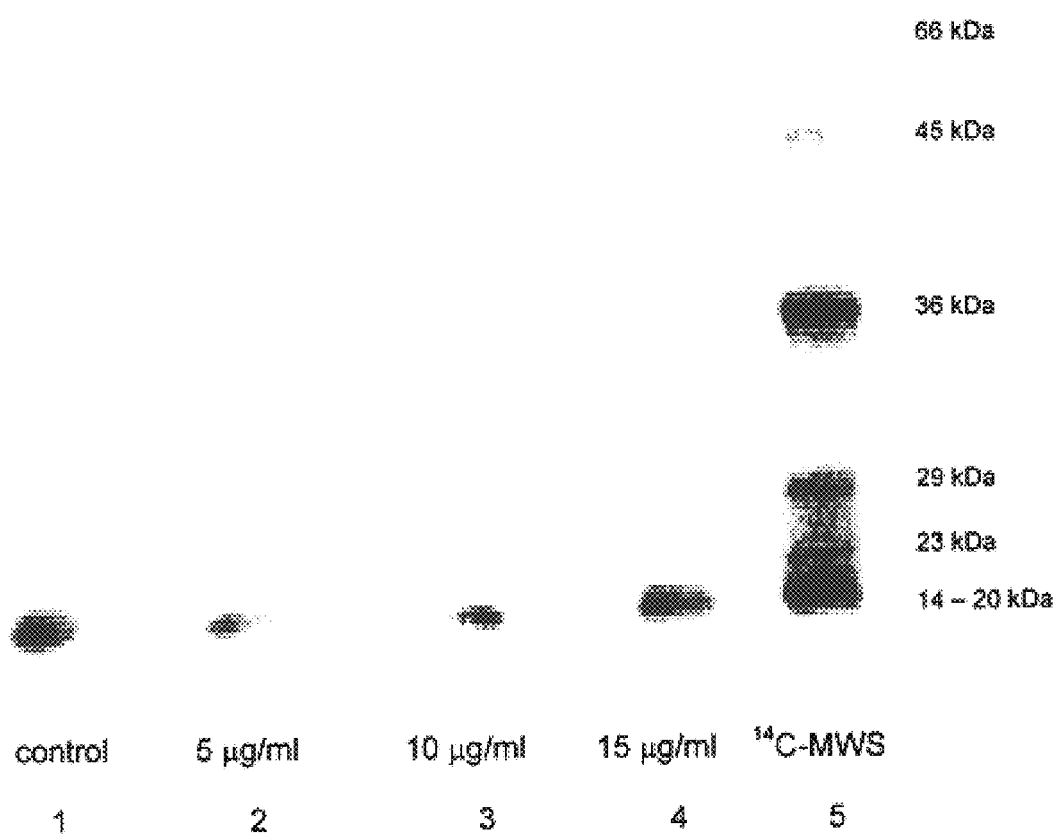
FIG. 5 is an autoradiogram that depicts the relative amount of $^3$H-farnesylated Ras-protein. Lane 1 is in the absence of dimethylaminoarglabin hydrochloride. Lanes 2–4 are in the presence of 5 μg/ml, 10 μg/ml and 15 μg/ml dimethylaminoarglabin hydrochloride, respectively. Lane 5 contains $^{14}$C-labeled marker.

FIG. 5 is an autoradiogram that indicates the amount of the labeled farnesyl moiety that was transferred to Ras, a 21 kDa protein. Dimethylaminoarglabin hydrochloride inhibited the transfer of the farnesyl moiety to Ras at all concentrations. Maximal inhibition was observed at 5 μg/ml. It is hypothesized that at higher concentrations, the plasma membranes of the cells become leaky and the drug and its metabolites pass through the membrane.

Example 7
Effect of ATP on Farnesylation

Figure 6:
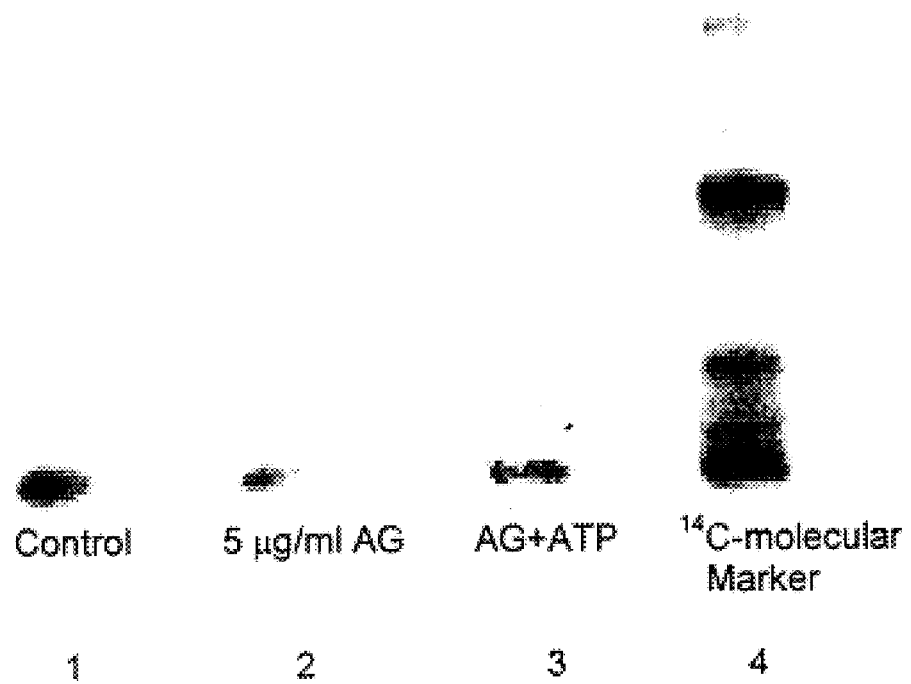
FIG. 6 is an autoradiogram that depicts the relative amount of $^3$H-farnesylated Ras-protein. Lane 1 is in the absence of dimethylaminoarglabin hydrochloride. Lane 2 is from a 12-hour incubation of 5 μg/ml dimethyaminoarglabin hydrochloride with Ras-transfected NIH3T3 cells. Lane 3 is from an incubation of dimethylaminoarglabin hydrochloride and ATP with a cell lysate. Lane 4 contains $^{14}$C-labeled marker.
Figure 7:
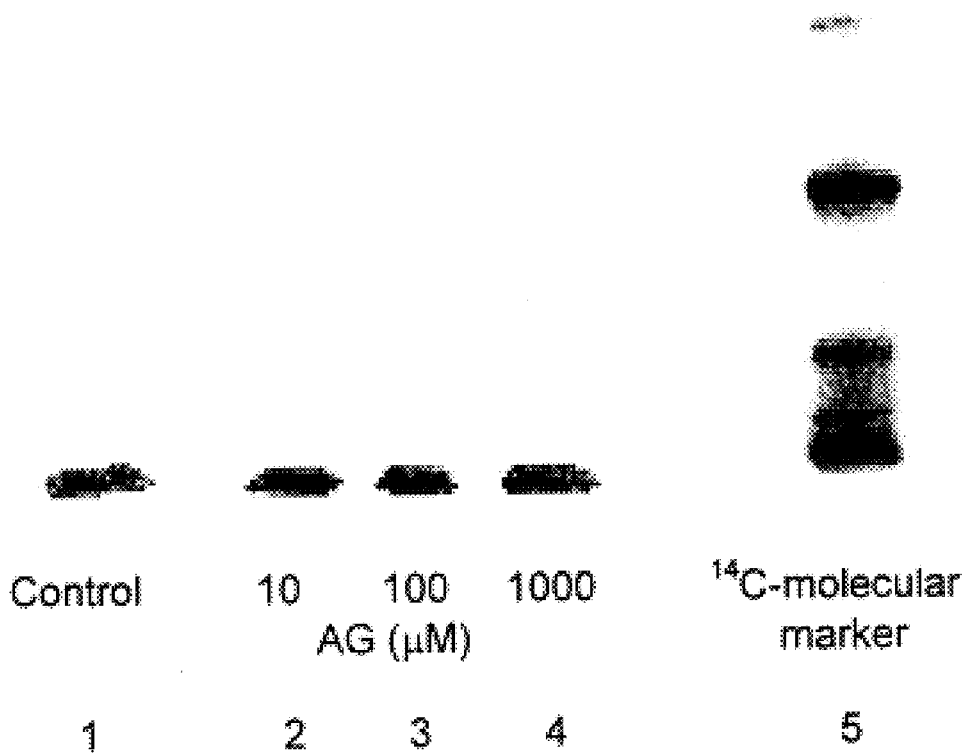
FIG. 7 is an autoradiogram that depicts that ATP is necessary for dimethylaminoarglabin hydrochloride to inhibit farnesylation. Lane 1 is in the absence of dimethylaminoarglabin hydrochloride. Lanes 2–4 are in the presence of 10, 100, and 1000 μM dimethylaminoarglabin hydrochloride, respectively. Lane 5 contains $^{14}$C-labeled marker.

Lysates of Ratransfected NIH3T3 cells grown in the absence of drug were prepared as described in Example 4. In one group, 200 μM of dimethylaminoarglabin hydrochloride and 200 μM ATP were incubated with the lysate at 37° C. for 40 minutes. In a second group, 5 μg/ml of dimethylaminoarglabin hydrochloride was incubated with Rastected NIH3T3 cells for 12 hours prior to preparation of the lysate. No drug was added to the control group. After the incubation period, H-ras protein and $^3$H-famesylpyrophosphate were added to the lysates as described in Example 4. FIG. 6 is an autoradiogram that indicates the relative amounts of the famesyl group that was transferred to the Ras proteins. As indicated in FIG. 6, the amount of famesylated Ras proteins was similar when cells were incubated with diinethylaminoarglabin hydrochloride and ATP just prior to assaying and when cells were incubated with dirnethylaminoarglabin hydrochloride without added ATP for 12 hours, suggesting that dimethylaminoarglabin hydrochloride is metabolized. When dimethylaminoarglabin hydrochloride was incubated with lysate in the absence of ATP, just prior to assaying, FPT activity was not inhibited (FIG. 7).

Figure 8:
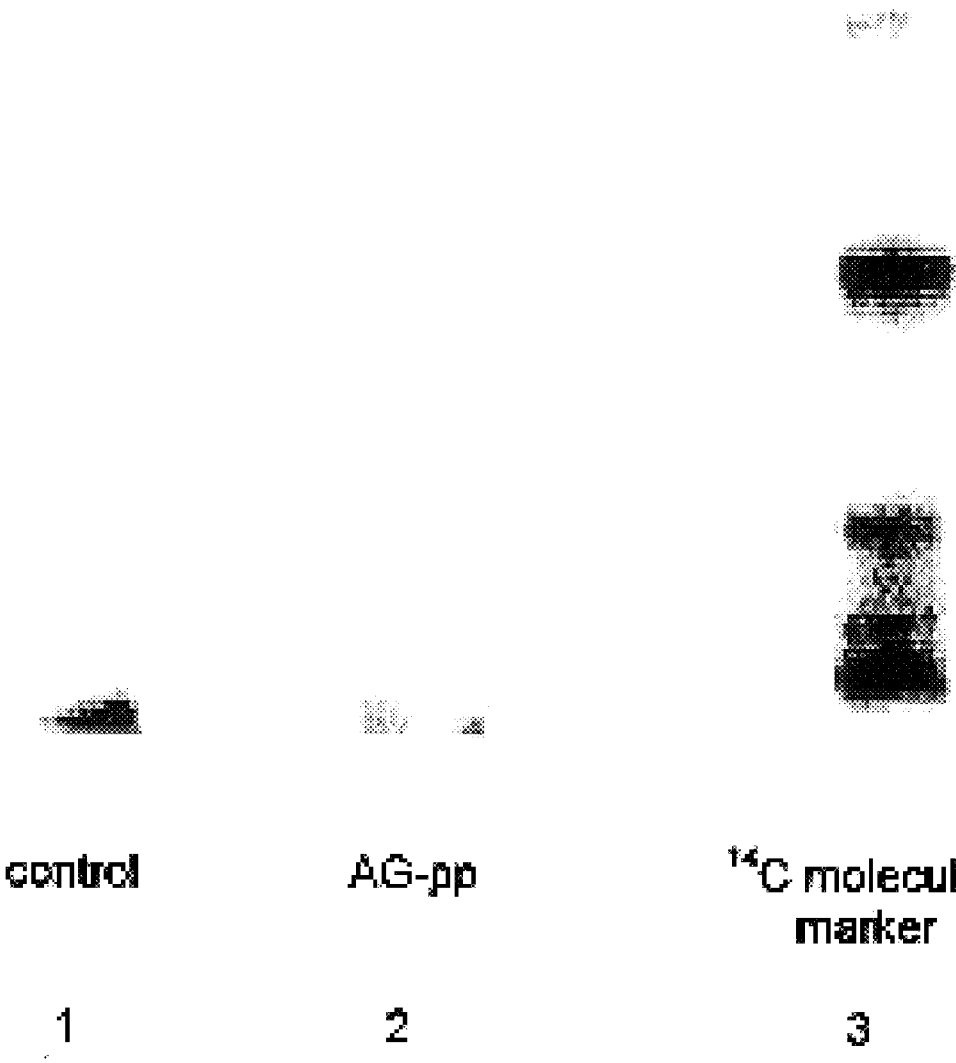
FIG. 8 is an autoradiogram that depicts the effect of phosphorylated-dimethylaminoarglabin hydrochloride on famesylation of Ras-proteins. Lane 1 is in the absence of diinethylaminoarglabin hydrochloride. Lane 2 is phosphorylated dimethylaminoarglabin hydrochloride. Lane 3 contains $^{14}$C-labeled marker.

To verify the role of the phosphorylated dimethyiarinoarglabin hydrochloride product, the phosphorylated form was obtained by incubating 20 mM Tris-HCl, pH 7.5, 10 mM $MgCl_2$, 200 mM ATP, 20 mM dimethylaminoarglabin 0.5 mg/ml S10 for 40 minutes at 37° C. Phosphorylated product was isolated by centrifugation through ultrafree-20 (Millipore) at 2,500×g for 30 minutes. The filtrate was lyophilized and dissolved in a small volume of water and tested for a inhibition of famesyltransferase using the assay described above. Product obtained in this manner prevented farnesylation of Ras proteins (FIG. 8).

Example 8
ATP Bioluminescence Assay

The effect of ATP on the activity of dimethylaminoarglabin was assessed using an ATP bioluminescence assay that provides a quantitative determination of ATP in a sample. he assay employs two enzymatic reactions that run in parallel. In the first reaction, ATP, luciferin and oxygen form AMP, pyrophosphate, oxyluciferin, carbon dioxide and light in the presence of luciferase. In a second reaction, sesquiterpene γ-lactone and ATP form phosphosesquiterpene in the presence of a lysate. Liver lysates and lysates from Ras-transfected NIH3T3 cells both provide the necessary FPT. ATP can interact with luciferin and the sesquiterpene compounds, but light is only detected when ATP reacts with luciferin.

In this experiment, 50 nM ATP, 50 μM Arglabin or mevalonolactone, 20 mg of S10 lysate and luciferase-luciferin solution were mixed in a final volume of 200 μl. After a 10 minute incubation at room temperature, the intensity of the resultant chemiluminescence was measured in a Beckman liquid scintillation counter as described by Ilahl, L. -A et al., (1986), Anal. Biochem. 155:177–181.

Figure 9:
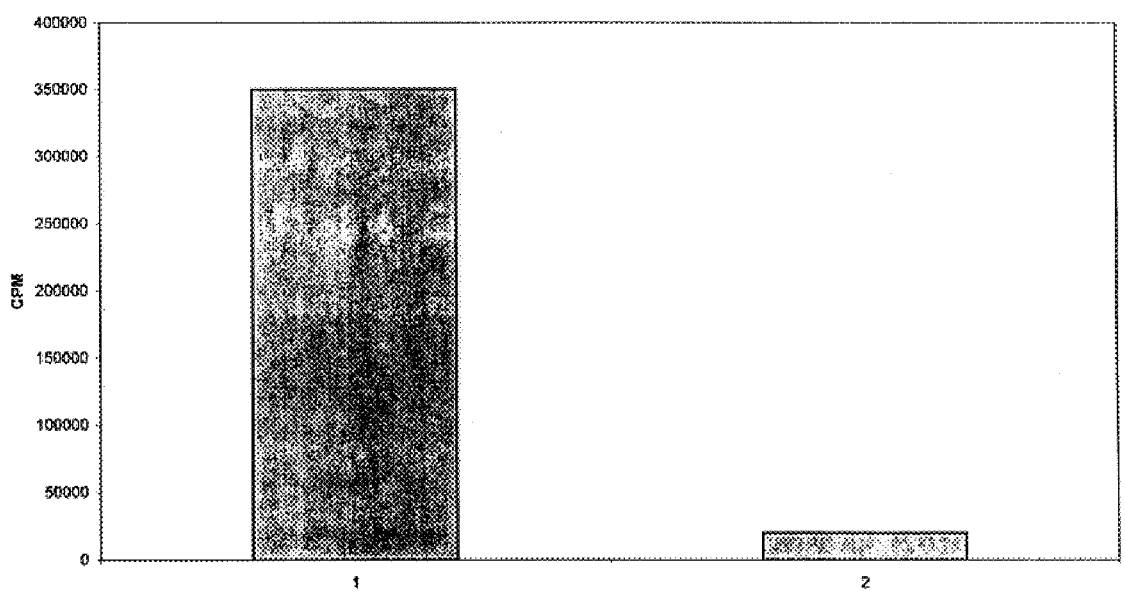
FIG. 9 is a graph that depicts the amount of bioluminescence after incubating an NIH3T3 cell lysate with dimethylaminoarglabin hydrochloride. The first bar is the control incubated in the absence of drug. The second bar is in the presence of drug.
Figure 10:
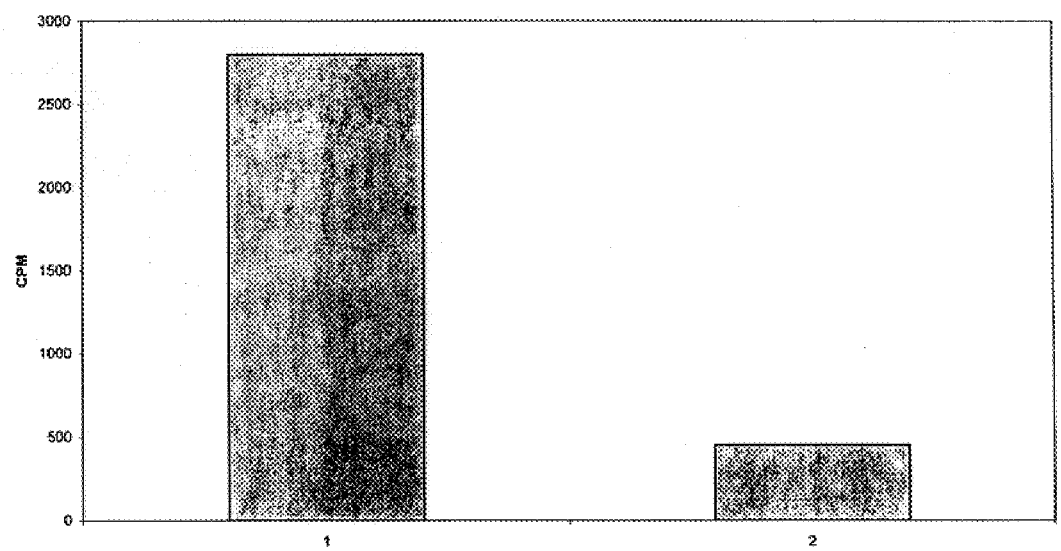
FIG. 10 is a graph that depicts the amount of bioluminescence after incubation of a liver lysate with dimethylaminoarglabin hydrochloride. The first bar is the control incubated in the absence of drug. The second bar is in the presence of drug.

As shown in FIG. 9, incubation of the lysate from Ras-transfected NIH3T3 cells with dimethylaminoarglabin hydrochloride (bar 2) resulted in about 20 times less light than with the control lacking drug (bar 1). Similar results were observed with the liver lysate (FIG. 10), although the overall amount of light was about 13 times less.

As an additional control, the ATP bioluminescence assay was repeated with mevalonolactone, a compound that is known to be phosphorylated (FIGS. 11 and 12). After incubation of mevalonolactone with the lysate from Ras-transfected NIH3T3 cells, a similar reduction in light was observed with mevalonolactone (triangles) and dimethylaminoarglabin hydrochloride (squares) as compared to the control (circles) (FIG. 11). When a lysate from liver was substituted, mevalonolactone had an intermediate effect between control and dimethylaminoarglabin (FIG. 12). Arglabin (squares) and dimethylaminoarglabin hydrochloride (triangles) (FIG. 13) were each phosphorylated when incubated with lysates from Ras-transfected NIH3T3 cells.

Other sesquiterpene lactones, including estafiatin, estafiatin dimethylamino hydrochloride, inuchinenolide C, inuchinenolide C dimethylamino hydrochloride, grosshemin, grosshemin dimethylamino hydrochloride, and grosshemin acetate dimethylamino hydrochloride, were tested and produced similar results.

Example 9

Chemical Synthesis and Purification of Phosphorylated Dimethylaminoarglabin

Phosphorylated dimethylaminoarglabin hydrochloride was chemically synthesized by reacting 7 ml of 57 mM dimethylaminoarglabin hydrochloride in 0.9% NaCl with 2 ml of 200 mM ATP in 10 mM $KHCO_3$, pH 7.0 for 1.5 hours at 70° C. Crystals of the phosphorylated compound were precipitated by centrifligation and filtered with Whatman filter paper. The supernatant and the precipitate were analyzed by thin-layer chromatography (TLC) and ammonium molybdate staining.

Eastman chromatogram sheets were activated by drying at 70° C. followed by a wash in an 80:20 acetonitrile:water solution. Samples were separated by an 80:20 acetonitrile:water solution for two hours and stained in a 1% ammonium molybdate solution in 5% $H_2SO_4$ and 100 mM HCl. TLC plates were developed at 70° C. for five minutes. Dimethylaminoarglabin and phosphorylated dimethylaminoarglabin stained blue in color and had $R_f$ values of 0.45 and 0.95, respectively.

The absorbances of the phosphorylated dimethylaninoarglabin and non-phosphorylated dimethylaminoarglabin were assessed using a Shimadzu UV-visible spectrophotometer. A 1.5 ml sample of phosphorylated dimethylaminoarglabin or non-phosphorylated dimethylaminoarglabin, final concentration 0.3 mg/ml and 0.6 mg/ml respectively, in a 1% ammonium molybdate solution were assessed. Reactions were incubated at 70° C. for 10 minutes and then scanned from 320–800 mn. The diinethylaminoarglabin solution was purple in color and had a maximum absorbance at 554 nm. Phosphorylated dimethylaminoarglabin was blue in color and had a maximum absorbance at 380 nm.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for inhibiting farnesyl-protein transferase activity, comprising contacting a cell with an amount of a sesquiterpene lactone effective to inhibit farnesyl-protein transferase activity of said cell, said sesquiterpene lactone having formula A,

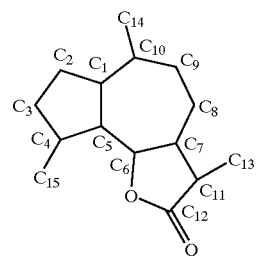

wherein:

$C_1$ is further bonded to hydrogen, hydroxy, short chain alkanoyloxy, or together with $C_2$ or $C_{10}$ form a double bond or an epoxide;

$C_2$ is further bonded to at least one of hydrogen, hydroxy, oxo, short chain alkanoyloxy, and together with $C_1$ or $C_3$ form a double bond or an epoxide;

$C_3$ is further bonded to at least one of hydrogen, oxo, and together with $C_2$ or $C_4$ form a double bond or an epoxide;

$C_4$ is further bonded to hydrogen, bydroxy, short chain alkanoyloxy, or together with $C_3$, $C_5$, or $C_{15}$ form an epoxide or a double bond;

$C_5$ is further bonded to hydrogen, hydroxy, short chain alkanoyloxy, or together with $C_4$ form an epoxide or a double bond;

$C_6$ is further bonded to hydrogen;

$C_7$ is further bonded to hydrogen or together with $C_{11}$ form a double bond;

$C_8$ is further bonded to at least one of hydrogen, hydroxy, and short chain alkanoyloxy;

$C_9$ is further bonded to at least one of hydrogen, and together with $C_{10}$ form a double bond;

$C_{10}$ is further bonded to hydrogen, hydroxy, short chain alkanoyloxy, together with $C_1$ or $C_{14}$ form an epoxide, or together with $C_1$, $C_9$, or $C_{14}$ form a double bond;

$C_{11}$ is further bonded to hydrogen, hydroxy, hydroxymethyl, or together with $C_7$ or $C_{13}$ form a double bond;

$C_{13}$ is further bonded to at least one of hydrogen, an optionally substituted alkylamino salt, and together with $C_{11}$ form a double bond;

$C_{14}$ is further bonded to at least one of hydrogen and together with $C_{10}$ form an epoxide or a double bond; and $C_{15}$ is further bonded to at least one of hydrogen and together with $C_4$ form an epoxide or a double bond.

2. A method for inhibiting farnesyl-protein transferase activity, comprising contacting a cell with an amount of a sesquiterpene lactone effective to inhibit farnesyl-protein transferase activity of said cell, said sesquiterpene lactone having formula B,

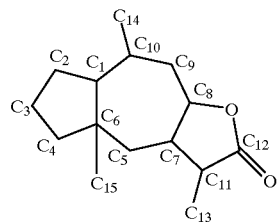

B wherein:

- $C_1$ is further bonded to hydrogen, hydroxy, short chain alkanoyloxy, or together with $C_2$ or $C_{10}$ form a double bond or an epoxide;
- $C_2$ is further bonded to at least one of hydrogen, hydroxy, oxo, short chain alkanoyloxy, and together with $C_1$ or $C_3$ form a double bond or an epoxide;
- $C_3$ is further bonded to at least one of hydrogen, oxo, and together with $C_2$ or $C_4$ form a double bond or an epoxide;
- $C_4$ is further bonded to at least one of hydrogen, hydroxy, short chain alkanoyloxy, and together with $C_3$ form an epoxide or a double bond;
- $C_6$ is further bonded to at least one of hydrogen, hydroxy, and short chain alkanoyloxy;
- $C_7$ is further bonded to hydrogen or together with $C_{11}$ form a double bond;
- $C_8$ is further bonded to hydrogen;
- $C_9$ is further bonded to at least one of hydrogen and together with $C_{10}$ form a double bond;
- $C_{10}$ is further bonded to hydrogen, hydroxy, short chain alkanoyloxy, together with $C_1$ or $C_{14}$ form an epoxide, or together with $C_1$, $C_9$, or $C_{14}$ form a double bond;
- $C_{11}$ is further bonded to hydrogen, hydroxy, hydroxymethyl, or together with $C_7$ or $C_{13}$ form a double bond;
- $C_{13}$ is further bonded to at least one of hydrogen, an optionally substituted alkylamino salt, and together with $C_{11}$ form a double bond;
- $C_{14}$ is further bonded to at least one of hydrogen and together with $C_{10}$ form an epoxide or a double bond; and
- $C_{15}$ is further bonded to three hydrogens.

* * * * *